US011419962B2

(12) United States Patent
Williams et al.

(10) Patent No.: US 11,419,962 B2
(45) Date of Patent: *Aug. 23, 2022

(54) SPHEROIDS INCLUDING BIOLOGICALLY-RELEVANT MATERIALS AND RELATED METHODS

(71) Applicant: UNIVERSITY OF LOUISVILLE RESEARCH FOUNDATION, INC., Louisville, KY (US)

(72) Inventors: Stuart K. Williams, Louisville, KY (US); Brian C. Gettler, Louisville, KY (US); Joseph S. Zakhari, Louisville, KY (US); Piyani S. Gandhi, Louisville, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/312,042

(22) PCT Filed: Jun. 27, 2017

(86) PCT No.: PCT/US2017/039483
§ 371 (c)(1),
(2) Date: Dec. 20, 2018

(87) PCT Pub. No.: WO2018/005477
PCT Pub. Date: Jan. 4, 2018

(65) Prior Publication Data
US 2019/0381213 A1    Dec. 19, 2019

Related U.S. Application Data

(60) Provisional application No. 62/422,694, filed on Nov. 16, 2016, provisional application No. 62/354,929, filed on Jun. 27, 2016.

(51) Int. Cl.
| | |
|---|---|
| *A61L 27/38* | (2006.01) |
| *C12N 5/0775* | (2010.01) |
| *A61L 27/52* | (2006.01) |
| *A61L 27/54* | (2006.01) |
| *A61L 27/56* | (2006.01) |
| *C12N 5/0735* | (2010.01) |

(52) U.S. Cl.
CPC .......... *A61L 27/52* (2013.01); *A61L 27/3834* (2013.01); *A61L 27/54* (2013.01); *A61L 27/56* (2013.01); *C12N 5/0606* (2013.01); *C12N 5/0667* (2013.01); *A61L 2300/62* (2013.01); *C12N 2513/00* (2013.01); *C12N 2533/30* (2013.01)

(58) Field of Classification Search
CPC ...... A61L 27/52; A61L 27/3834; A61L 27/54; A61L 27/56; A61L 2300/62; C12N 5/0606; C12N 5/0667; C12N 2533/30; C12N 2513/00
See application file for complete search history.

(56) References Cited

U.S. PATENT DOCUMENTS 6,284,503 B1 * 9/2001 Caldwell ............... C07C 281/02
435/181

FOREIGN PATENT DOCUMENTS

| KR | 101555239 B1 * | 9/2015 | ............... C12M 3/00 |
| WO | WO2015027086 A1 * | 2/2015 | ............... C12N 5/071 |

OTHER PUBLICATIONS

Lee et al. English machine translation of KR101555239. downloaded from IP.com, p. 1-11 (Year: 2015).*
Shin et al. Bio-Inspired Extreme Wetting Surfaces for Biomedical Applications. Materials 2016, 9, 116, p. 1-26 (Year: 2016).*
Zhang et al. Inkjet printing for direct micropatterning of a superhydrophobic surface: toward biomimetic fog harvesting surfaces. J. Mater. Chem. A, 2015, 3, 2844-2852 (Year: 2015).*
Lee et al.: "Spheroform: Therapeutic Spheroid-Forming Nanotextured Surfaces Inspired by Desert Beetle Physostema cribripes", Advance Healthcare Materials, vol. 4, pp. 511-515, 2015.

* cited by examiner

*Primary Examiner* — Taeyoon Kim
(74) *Attorney, Agent, or Firm* — WCF IP

(57) ABSTRACT

A method of making a spheroid is provided that includes the step of providing a suspension having one or more biologically-relevant materials dispersed within a biocompatible medium. An amount of a hydrophilic material is deposited on a defined area of a super-hydrophobic surface, and a droplet of the suspension is bioprinted onto the hydrophilic material positioned on the super-hydrophobic to thereby create the spheroid.

19 Claims, 15 Drawing Sheets

SPHEROIDS INCLUDING BIOLOGICALLY-RELEVANT MATERIALS AND RELATED METHODS

RELATED APPLICATIONS

This application claims priority from U.S. Provisional Application Ser. No. 62/354,929, filed Jun. 27, 2016, and U.S. Provisional Application Ser. No. 62/422,694, filed Nov. 16, 2016, the entire disclosures of which are incorporated herein by this reference.

TECHNICAL FIELD

The presently-disclosed subject matter generally relates to spheroids including biologically relevant materials and related methods. In particular, certain embodiments of the presently-disclosed subject matter relate to spheroids including biologically relevant materials and methods of making such spheroids whereby a suspension containing one or more biologically-relevant materials is bioprinted onto a super-hydrophobic surface.

BACKGROUND

The use of three-dimensional environments for cell culture provides a more physiologically-relevant system for in vitro modeling of cell behavior and for the creation of constructs for subsequent implantation. In the body, tissues are composed of multiple cell types and cells are organized in specific spatial arrangements providing orientation of cells into geometries specific to organ functions. The study of cell function in vitro, originally utilizing cells grown on tissue culture surfaces (e.g. glass and plastic), has now transitioned to three-dimensional (3D) cultures of cells that are often embedded in collagen gels. Coordinately, investigators have evaluated the ability of two- and three-dimensional cell cultures to undergo the spontaneous formation of spheroids during culture. Epithelial and endothelial organoid cultures have been established in this way. In those procedures, embryonic stem cells were cultured as hanging drops and allowed to form embryoid bodies (EBs). Spheroid culture strategies have since progressed to include endothelium, representing cells of the vasculature, a common cellular component of all complex tissues. And recently, complex three-dimensional tissue constructs containing parenchymal cells and vascular cells have been implanted in experimental models. Each of those studies show that functional tissue organoids can be constructed in vitro, implanted in tissue with evidence of vascular integration between implanted and recipient circulations and with evidence that the organoids can provide restoration of tissue function.

To assist in the vascular integration of three-dimensional tissue constructs, several studies have made use of an adipose-derived stromal vascular fraction (SVF). The adipose-derived SVF is a heterogeneous population of cells with a multitude of regenerative properties for in vivo and clinical applications. The current primary mode of delivery for SVF, and many other stem and regenerative cell populations, is the direct injection of cells suspended in solution. One major shortcoming of direct injection of SVF, however, is the observed lack of retention of cells at the site of implantation. As such, the assembly of cells into aggregates, either by direct encapsulation or culture-dependent self-aggregation, has been proposed to increase retention of cells upon injection. In this regard, SVF has previously been embedded within a scaffold or encapsulated within a variety of matrix hydrogels for in vitro applications and these encapsulated aggregates have increased SVF localization and retention. Previous work toward SVF cell aggregation has also included the use of alginate encapsulation to form spheroids and other 3D culture of SVF in collagen gels.

Currently, the creation of spheroids has fallen primarily under the nominal categories of cellular spheroids, surface seeded spheroids, and encapsulated spheroids. Again though, such cellular spheroids are typically created by hanging drop methods or otherwise rely on the mechanism of cells self-aggregating due to lack of other adhesion points. Cells can aggregate spontaneously utilizing adhesion points to support migration to a central mass or aggregate of cells. This production process takes several days to produce spheroids and suffers from inconsistencies that are heavily magnified by cell proliferation rates. Surface seeded spheroids are pre-fabricated with the biopolymer of choice and then incubated with the cells of choice to allow cell migration driven seeding. This production strategy has a very broad range of applications so long as the biomaterial of choice can be prefabricated. The drawback of prefabricated spheroids is that the cell seeding is migration/adhesion based and therefore is primarily limited to the spheroid surface rather than the entire volume of the spheroid limiting the spheroid loading capacity. The third strategy of encapsulated spheroids revolves around the idea of mixing cells into a suspension and then allowing that suspension to become the scaffold/hydrogel of choice. Encapsulation based spheroids have the advantage of being able to utilize the full volume of the spheroids for cell carrying and the ability to be produced in less than a day. This strategy has been very biomaterial specific, however, and, in the case of collagen, has frequently required the use of a support material such as alginate that alters the mechanical properties and by proxy some of the biological properties that made the original biomaterial so appealing.

In short, the formation of three-dimensional cell and tissue constructs has yet to be fully realized. Accordingly, any improvements in the production of such complex biological structures would be both highly desirable and beneficial.

SUMMARY

The presently-disclosed subject matter meets some or all of the above-identified needs, as will become evident to those of ordinary skill in the art after a study of information provided in this document.

This summary describes several embodiments of the presently-disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this summary or not. To avoid excessive repetition, this summary does not list or suggest all possible combinations of such features.

In some implementations of the presently-disclosed subject matter, methods of making spheroids including biologically-relevant materials are provided. In one implementation, a method of making a spheroid including one or more biologically-relevant materials is provided in which a suspension is first created or provided, where the suspension includes one or more biologically-relevant materials dispersed within a biocompatible medium. An amount of a hydrophilic material is then deposited in a defined area and/or in a defined amount onto a super-hydrophobic surface of a suitable substrate. In some implementations, the hydrophilic material deposited on the super-hydrophobic surface is comprised of a polyoxyethylene-polyoxypropylene block copolymer. In some implementations, the super-hydrophobic surfaces utilized in accordance with the presently-disclosed subject matter have a water contact angle of greater than about 150°, such as, in some implementations, a water contact angle of about 150° to about 170°.

Regardless of the particular hydrophilic materials and/or water contact angles of the super-hydrophobic surfaces utilized in an exemplary method of the presently-disclosed subject matter, once the suspension and substrate are produced, a droplet of the suspension is then bioprinted (e.g., direct write printed) directly onto the hydrophilic material positioned on the super-hydrophobic surface to thereby produce a spheroid including the biologically-relevant materials. Subsequent to bioprinting the suspension, the resulting spheroids can then be incubated at physiological temperatures for a period of time while maintaining their spheroid shape. In some implementations, if desired, the spheroids can then be further cultured in a cell culture medium.

In some implementations of the presently-disclosed methods, the one or more biologically-relevant materials included in an exemplary spheroid are comprised of magnetic beads, stromal vascular fraction cells, stem cells, one or more relevant cells, groups of cells or tissues, or combinations thereof. For example, in some implementations, a spheroid can be produced including stromal vascular fraction cells in combination with one or more relevant cells, such as pancreatic islet cells. In some implementations, the one or more biologically-relevant materials can thus comprise stromal vascular fraction cells. In some implementations, the one or more biologically-relevant materials comprises one or more islet cells.

With respect to the biocompatible medium used to form the suspensions utilized in the presently-disclosed methods, in some implementations, the biocompatible medium comprises a hydrogel. In some implementations, the hydrogel is comprised of a material selected from the group consisting of agarose, alginate, collagen, a polyoxyethylene-polyoxypropylene block copolymer; silicone, polysaccharide, polyethylene glycol, and polyurethane. In some implementations, the hydrogel is comprised of collagen type I.

Further features and advantages of the presently-disclosed subject matter will become evident to those of ordinary skill in the art after a study of the description, figures, and non-limiting examples in this document.

BRIEF DESCRIPTION OF THE DRAWINGS

FIG. 6B shows an approximately 20° perspective shift compared to the top view shown in FIG. 6A.

FIG. 7A is a phase contrast image illustrating an SVF/islet spheroid immediately after printing and polymerization. FIG. 7B is an image of a spheroid illustrating a 7 day SVF/Islet spheroid. Spheroids undergo contraction during culture. The scale bar is=500 microns.

FIG. 9A is a phase contrast image following 11 days in culture illustrating SVF cell distribution within spheroid. Bar=100 microns. FIG. 9B is a phase contrast image following 12 days in culture illustrating the onset of contraction. Bar=100 microns. FIG. 9C is a phase contrast image following 8 days in culture Bar=50 microns. FIG. 9D is a phase contrast image following 11 days in culture illustrating more extensive branch formation compared to day 8 spheroids. Bar=50 microns. FIG. 9E is a confocal microscopic image of a SVF laden collagen I spheroid after 14 days stained with the endothelial specific lectin Griffonia simplicifoli, GS-1 (green), alpha smooth muscle cell actin, ($\alpha$-SMA) (red), and nuclear stain, RedDot (blue). Bar=100 microns. FIGS. 9F and 9G are two higher magnification perspectives of the vessel-like structure in FIG. 6E co-labeled with GS-1 and $\alpha$-SMA demonstrating branching structures as demarcated by arrows. Bar=50 microns.

DESCRIPTION OF EXEMPLARY EMBODIMENTS

Figure 1A:
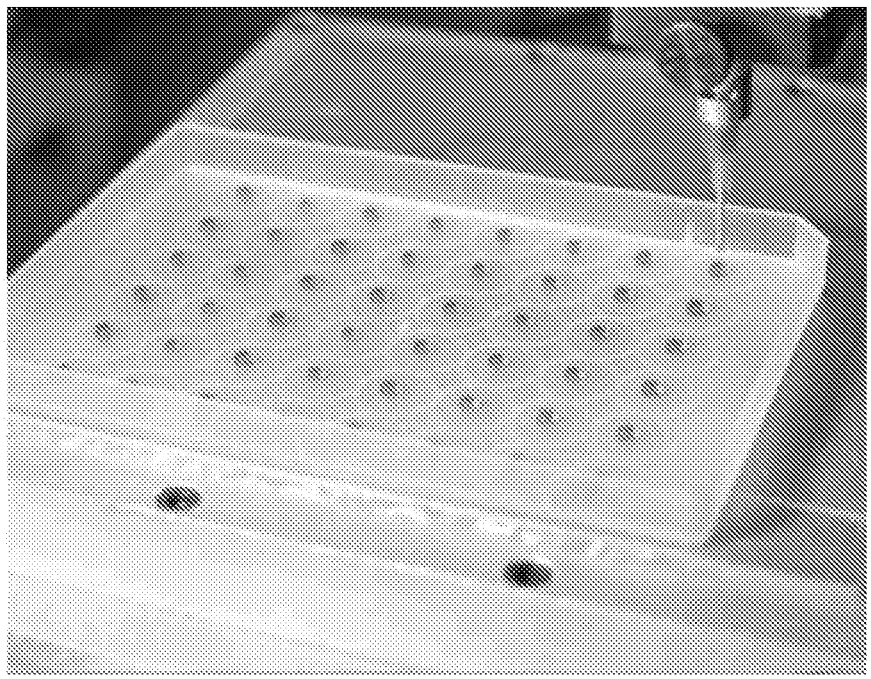
FIGS. 1A-1D includes images showing stromal vascular fraction (SVF) laden collagen I spheroids immediately after bioprinting on a biphilic surface (FIGS. 1A-1C) and a schematic diagram showing a cross-section of a biphilic surface and a collagen I spheroid (FIG. 1D).

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

While the terms used herein are believed to be well understood by those of ordinary skill in the art, certain definitions are set forth to facilitate explanation of the presently-disclosed subject matter.

Unless defined otherwise, all technical and scientific terms used herein have the same meaning as is commonly understood by one of skill in the art to which the invention(s) belong.

All patents, patent applications, published applications and publications, GenBank sequences, databases, websites and other published materials referred to throughout the entire disclosure herein, unless noted otherwise, are incorporated by reference in their entirety.

Where reference is made to a URL or other such identifier or address, it understood that such identifiers can change and particular information on the internet can come and go, but equivalent information can be found by searching the internet. Reference thereto evidences the availability and public dissemination of such information.

Although any methods, devices, and materials similar or equivalent to those described herein can be used in the practice or testing of the presently-disclosed subject matter, representative methods, devices, and materials are described herein.

The present application can "comprise" (open ended) or "consist essentially of" the components of the present invention as well as other ingredients or elements described herein. As used herein, "comprising" is open ended and means the elements recited, or their equivalent in structure or function, plus any other element or elements which are not recited. The terms "having" and "including" are also to be construed as open ended unless the context suggests otherwise.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, "optional" or "optionally" means that the subsequently described event or circumstance does or does not occur and that the description includes instances where said event or circumstance occurs and instances where it does not. For example, an optionally variant portion means that the portion is variant or non-variant.

The presently-disclosed subject matter is based, at least in part, on the discovery that three-dimensional (3D) bioprinting technology can be utilized in combination with a substrate having a super-hydrophobic surface to support the automated production of spheroids including biologically-relevant materials, including stromal vascular fraction (SVF) laden spheroids in collagen I gels. A limiting factor in the utilization of bulk collagen gels is the handling prior to and during implantation. Collagen I polymerization, from liquid to cross-linked hydrogel, typically occurs within a shape-holder such as a multi-well plate. Such a polymerized construct is then typically removed and handled manually with sterile equipment. However, handling, and any potential subsequent gel damage, is very difficult to regulate. In addition, while collagen gels have some elasticity, in vivo applications generally call for shapes that are irregular, and therefore require forcing a bulk gel to be either cut into sections or put under significant deformation to fit the necessary shape. Without wishing to be bound by any particular theory of mechanism, it was believed that those issues could be mitigated by unitizing collagen gels into small spheroids, and it was further believed that such collagen spheroids have the benefits of simplified handling in a fluid suspension and allow for precise spatial and dosing control to fit in vivo application requirements in a superior manner compared to cell suspension injections alone.

In some implementations of the presently-disclosed subject matter, methods of making a spheroid are thus provided. In some implementations, a method of making a spheroid is provided in which a hydrophilic material is first placed onto a defined area on the surface of a substrate where the surface of the substrate is super-hydrophobic. One or more biologically-relevant materials are then suspended within a biocompatible medium to create a suspension, and a droplet of the suspension is bio-printed onto the hydrophilic material. For instance, in one exemplary implementation of a method for making a spheroid of the presently-disclosed subject matter that makes use of direct-write printing as a form of bioprinting, a BioArchitecture Tool (BAT; see, e.g., U.S. Pat. No. 7,857,756; see also Smith, et al., Tissue Eng. 2004; 10:1566-1576, both of which are incorporated herein by this reference) is utilized that makes use of a computer-controlled stage, which not only permits independent X- and Y-axis translation, but also permits Z-axis movement of one or more translational print head/dispensing systems. In this regard, bioprinting parameters can first be scripted as printing instructions and then uploaded to the printing tool such that the printing tool (i.e., the BAT) can be used to produce a precise structure containing a suspension. In some implementations, by making use of such a printing tool, the size of a droplet printed by such a system can be controlled by controlling the size of the pen used to print the droplet and by controlling the pressure with which the droplet is extruded from the pen. In some embodiments, about a 15 gauge pen to about a 25 gauge pen and a pressure of about 2 psi to about 7 psi can be used to produce a droplet, or resulting spheroid as described in detail below, having a size of about 0.2 mm to about 5 mm in diameter. In some implementations, the droplets, or resulting spheroids, have a diameter of about 1 mm to about 5 mm, about 2 mm to about 4 mm, or about 3 mm to about 4 mm. In some implementations, the size of the droplets or spheroids is controlled by adjusting one or more parameters selected from the group consisting of: the viscosity of the suspension, the size of the delivery pen tip, the pressure used to extrude the suspension from the delivery pen, and the amount of time pressure is applied to the suspension in the delivery pen. Such parameters can readily be adjusted by those skilled in the art to produce a droplet or spheroid having a desired size.

As one exemplary implementation of a method for making a spheroid including one or more biologically-relevant materials, a spheroid is produced by first placing a suspension in the form of a cell suspension (e.g., a cell suspension comprised of a human stromal vascular fraction cell population mixed in collagen type I), in a delivery pen that is comprised of a hollow needle or tube-like structure. Extrusion of the biological suspension from the delivery pen is then controlled by increasing the pressure in the delivery pen to a specific value, thereby causing a droplet to form. The delivery pen is then lowered toward a hydrophilic material placed on a superhydrophobic surface of a substrate at a predetermined rate (e.g., 5 mm/sec). Upon contacting the hydrophilic material, the suspended droplet is subsequently attracted to the hydrophilic material and is released from the pen to thereby form the spheroid atop the hydrophilic spot on the super-hydrophobic surface. In some implementations, subsequent to bioprinting the suspension, the resulting spheroids can then be incubated at physiological temperatures (e.g., 37° C.) for a period of time, such as a period of time sufficient to polymerize the biological medium being utilized. In some implementations, if desired, the spheroids can then be further cultured in a cell culture medium.

The term "suspension" is used herein to refer to a composition comprising biologically-relevant materials, including magnetic particles, cells, tissues, proteins, and the like that are dispersed within a biocompatible medium. A suitable biocompatible medium for use in accordance with the presently-disclosed subject matter can typically be formed from any biocompatible material that is a gel, a semi-solid, or a liquid, such as a low-viscosity liquid, at room temperature (e.g., 25° C.) and can be used as a three-dimensional substrate for cells, tissues, proteins, and other biological materials of interest. Exemplary materials that can be used to form a biocompatible medium in accordance with the presently-disclosed subject matter include, but are not limited to, polymers and hydrogels comprising collagen, fibrin, chitosan, MATRIGEL™ (BD Biosciences, San Jose, Calif.), polyethylene glycol, dextrans including chemically-crosslinkable or photo-crosslinkable dextrans, and the like, as well as electrospun biological, synthetic, or biological-synthetic blends. In some implementations, the biocompatible medium is comprised of materials that support endothelialization, see, e.g., U.S. Pat. Nos. 5,744,515 and 7,220,276, both of which are incorporated herein by reference. In some implementations, the biocompatible medium is comprised of a hydrogel.

The term "hydrogel" is used herein to refer to two- or multi-component gels comprising a three-dimensional network of polymer chains, where water acts as the dispersion medium and fills the space between the polymer chains. Hydrogels used in accordance with the presently-disclosed subject matter are generally chosen for a particular application (e.g., a particular spheroid) based on the intended use of the structure, taking into account the printing parameters that are to be used as well as the effect the selected hydrogel will have on the behavior and activity of the biological materials (e.g., cells) incorporated into the biological suspensions that are to be placed in the structure. Exemplary hydrogels of the presently-disclosed subject matter can be comprised of polymeric materials including, but not limited to: alginate, collagen (including collagen types I and VI), fibrinogen, elastin, keratin, fibronectin, proteoglycans, glycoproteins, polylactide, polyethylene glycol, polycaprolactone, polycolide, polydioxanone, polyacrylates, polyurethanes, polysulfones, peptide sequences, proteins and derivatives, oligopeptides, gelatin, elastin, fibrin, laminin, polymethacrylates, polyacetates, polyesters, polyamides, polycarbonates, polyanhydrides, polyamino acids carbohydrates, polysaccharides and modified polysaccharides, and derivatives and copolymers thereof as well as inorganic materials such as glass such as bioactive glass, ceramic, silica, alumina, calcite, hydroxyapatite, calcium phosphate, bone, and combinations of all of the foregoing. For additional information regarding the materials from which a hydrogel of the presently-disclosed subject matter may be comprised, see, e.g., U.S. Pat. Nos. 7,919,11, 6,991,652 and 6,969,480, each of which are incorporated herein by this reference.

With further regard to the hydrogels used to produce the spheroid, in some implementations, the hydrogel is comprised of a material selected from the group consisting of agarose, alginate, collagen type I, a polyoxyethylene-polyoxypropylene block copolymer (e.g., Pluronic® F127 (BASF Corporation, Mount Olive, N.J.)), silicone, polysaccharide, polyethylene glycol, and polyurethane. In some implementations, the hydrogel is comprised of alginate. In some implementations, the hydrogel is comprised of collagen type I.

Turning now to the biologically-relevant materials included in an exemplary suspension and used in accordance with the presently-disclosed subject matter, the phrase "biologically-relevant materials" is used herein to describe materials that are capable of being included in a biocompatible medium as defined herein and subsequently interacting with and/or influencing biological systems. For example, in some implementations, the biologically-relevant materials are magnetic beads (i.e., beads that are magnetic themselves or that contain a material that responds to a magnetic field, such as iron particles) that can be combined with a hydrogel and then bioprinted along with the hydrogel to produce spheroids having a defined size that can be used in the calibration of instrumentation or for the separation and purification of cells and tissues according to methods known to those skilled in the art. As another example, in other implementations, the biologically-relevant materials include one or more cells and tissues, such that combining the cells or tissues with an appropriate biocompatible medium results in the formation of a cell or tissue suspension. In some implementations, the biologically-relevant materials are comprised of stromal vascular fraction cells, stem cells, one or more relevant cells, or combinations thereof. In some implementations, the biologically-relevant materials are comprised of stromal vascular fraction cells.

With respect to the stromal vascular fraction cells used in accordance with methods of the presently-disclosed subject matter, the stromal vascular fraction cells are those that are typically obtained by enzymatically digesting an amount of adipose tissue obtained from a subject, followed by a period of centrifugation to pellet the stromal vascular fraction of the adipose tissue. In this regard, the stromal vascular fraction contains a number of cell types, including endothelial cells, smooth muscle cells, pericytes, preadipocytes, mesenchymal stem cells (MSCs), endothelial progenitor cells, T cells, B cells, mast cells, and adipose tissue macrophages, as well as small blood vessels or microvascular fragments found within the stromal vascular fraction. For further explanation and guidance regarding the disassociation of adipose tissue to produce a stromal vascular fraction, see, e.g., U.S. Pat. No. 4,820,626, the entire contents of which are incorporated herein by this reference. In some embodiments, incomplete digestion of adipose tissue can also be used to yield adipose microvascular fragments, see, e.g., U.S. Pat. No. 7,029,838, which is also incorporated herein by reference.

With respect to the stem cells that can be utilized in accordance with the methods of the present invention, as used herein, the term "stem cells" refers broadly to traditional stem cells, progenitor cells, preprogenitor cells, precursor cells, reserve cells, and the like. Exemplary stem cells include, but are not limited to, embryonic stem cells, adult stem cells, pluripotent stem cells, neural stem cells, liver stem cells, muscle stem cells, muscle precursor stem cells, endothelial progenitor cells, bone marrow stem cells, chondrogenic stem cells, lymphoid stem cells, mesenchymal stem cells, hematopoietic stem cells, central nervous system stem cells, peripheral nervous system stem cells, and the like. Descriptions of stem cells, including methods for isolating and culturing them, may be found in, among other places, Embryonic Stem Cells, Methods and Protocols, Turksen, ed., Humana Press, 2002; Weisman et al., Annu. Rev. Cell. Dev. Biol. 17:387-403; Pittinger et al., Science, 284:143-47, 1999; Animal Cell Culture, Masters, ed., Oxford University Press, 2000; Jackson et al., PNAS 96(25): 14482-86, 1999; Zuk et al., Tissue Engineering, 7:211-228, 2001; and U.S. Pat. Nos. 5,559,022, 5,672,346 and 5,827, 735. Descriptions of stromal cells, including methods for isolating them, may be found in, among other places, Prockop, Science, 276:71-74, 1997; Theise et al., Hepatology, 31:235-40, 2000; Current Protocols in Cell Biology, Bonifacino et al., eds., John Wiley & Sons, 2000; and U.S. Pat. No. 4,963,489. One of ordinary skill in the art will understand that the stem cells and/or stromal cells that are selected for inclusion in a tissue construct are typically selected when such cells are appropriate for the intended use of a particular construct.

Finally, with respect to the relevant cells that can be utilized in accordance with the methods of the present invention, the term "relevant cells," as used herein refers to cells that are appropriate for incorporation into a spheroid of the presently-disclosed subject matter, based on the intended use of that spheroid. In some embodiments, the term "relevant cells" can be used interchangeable with the term "regenerative cells" as the relevant cells described herein have the ability to form a functional tissue following implantation. For example, relevant cells that are appropriate for the repair, restructuring, or repopulation of particular damaged tissue or organ will typically include cells or groups of cells that are commonly found in that tissue or organ. In that regard, exemplary relevant cells that can be incorporated into spheroids of the presently-disclosed subject matter include neurons, cardiomyocytes, myocytes, vascular and/or gastrointestinal smooth muscle cells, chondrocytes, pancreatic acinar cells, islets of Langerhans, islet beta cells, osteocytes, hepatocytes, Kupffer cells, fibroblasts, myoblasts, satellite cells, endothelial cells, adipocytes, preadipocytes, biliary epithelial cells, and the like. These types of cells may be isolated and used immediately or subjected to culture by conventional techniques known in the art. Exemplary techniques can be found in, among other places; Freshney, Culture of Animal Cells, A Manual of Basic Techniques, 4th ed., Wiley Liss, John Wiley & Sons, 2000; Basic Cell Culture: A Practical Approach, Davis, ed., Oxford University Press, 2002; Animal Cell Culture: A Practical Approach, Masters, ed., 2000; and U.S. Pat. Nos. 5,516,681 and 5,559, 022. In some implementations, the biologically-relevant cells comprise pancreatic islet cells (e.g. beta cells) or the entire intact islet.

Regardless of the particular type of biologically-relevant materials that are combined with a biocompatible medium in accordance with the presently-disclosed subject matter, as indicated above, once the biologically-relevant materials are combined with a biocompatible medium, a droplet of the resulting suspension is then bioprinted onto a hydrophilic material placed on a superhydrophobic surface. In this regard, when the suspension reaches room temperature, the suspension will typically gelate and form a spheroid having a more stable geometry. To maintain the geometry of the droplets or spheroids after extrusion but before polymerization or gelation, however, and as noted above, the presently-disclosed methods make use of a substrate having a super-hydrophobic surface.

The term "super-hydrophobic" is used herein to refer to substrates exhibiting a minimal attraction to water. Super-hydrophobic surfaces with typically exhibit the lotus effect such as what occurs when water droplets come into contact with, for example, lotus or taro leaves. Other naturally-occurring examples of super-hydrophobic surfaces supporting the formation of water droplets can be found in, for example, the fogstand beetle (*Stenocara gracilipes*), which is found in the Namib Desert. In this regard, such super-hydrophobic substrates or surfaces will typically have a water contact angle, or the angle where a liquid or vapor interface meets a solid surface as measured through the liquid, of greater than about 1550°. In some implementations, the super-hydrophobic surfaces used herein have water contact angles of greater than 150°. In some implementations, the water contact angle of an exemplary super-hydrophobic surface is about 150° to about 170°. Numerous super-hydrophobic surfaces having such water contact angles are known to those skilled in the art and can be present as a result of the particular substrate utilized or as a result of a coating applied to the substrates. For example, in some implementations, a super-hydrophobic surface can be produced by spraying a water repellant coating, such as NEVERWET™ (Rust Oleum, Vernon Hills, Ill.), onto a suitable substrate. Further examples, of super-hydrophobic surface coatings include, but are not limited to, silica, manganese oxide polystyrene ($MnO_2$/PS), zinc oxide polystyrene (ZnO/PS), precipitated calcium carbonate, perfluorobutanesulfonic acid, carbon nanotube structures, paraffin, polytetrafluoroethylene, wax, and the like.

As also noted above, in some implementations of the methods described herein, an amount of a hydrophilic material, i.e., a material having an increased affinity for water and typically having a water contact angle of less than about 90°, is placed onto a defined area of the hydrophobic surface. The amount of hydrophilic material and the area onto which the hydrophilic material is placed can, of course, vary depending on the spheroid being produced. In some implementations, however, about 2 µl to about 5 µl of a hydrophilic material is placed onto a hydrophobic surface to ensure that the spheroid attaches to the super-hydrophobic surface rather than remaining attached to printing pen. In some implementations, block copolymers, such as Pluronic® F127, having an amphiphilic block structure can be utilized as such copolymers are both hydrophilic and hydrophobic and are thus capable of adhering to both the hydrophobic surface and aqueous biocompatible media, such as collagen. Other hydrophilic materials capable of use in accordance with the present invention include, but are not limited to, other copolymers such as P 188, as well as other materials such are urethanes and silanes. In some embodiments, hydrophilic materials that are useful in the formation of spheroids provide adhesion characteristics that are reversible to allow removal of the spheroid. Such a reversal can be caused by, among other things, a change in temperature or solubilization of the hydrophilic substance in the aqueous phase of the spheroid.

Still further provided, in some embodiments of the presently-disclosed subject matter, are spheroids made according to the methods described herein. Without wishing to be bound by any particular theory or mechanism, it is believed that such spheroids are advantageous as: an in vitro assay of angiogenesis and vasculogenesis to screen drugs; a device (spheroid) that can be implanted into a patient to provide new blood flow to ischemic tissue; and a device (spheroid) that can be constructed using the adipose derived stem and regenerative cells and incorporates other parenchymal cells that can includes liver cells, muscle cells, fat cells, pancreatic cells including islets, brain cells, reproductive cells, kidney cells, and the like. Furthermore, it is believed that the presently-disclosed spheroids and methods allow for the production of a device that can be formed and implanted immediately without the need to subject material to tissue culture and without the need to utilize other additives (e.g. alginate) to support formation of a stable spheroid. It is also believed that the spheroids described herein support blood vessel formation in vitro.

The practice of the presently disclosed subject matter can employ, unless otherwise indicated, conventional techniques of cell biology, cell culture, molecular biology, transgenic biology, microbiology, recombinant DNA, and immunology, which are within the skill of the art. Such techniques are explained fully in the literature. See e.g., Molecular Cloning A Laboratory Manual (1989), 2nd Ed., ed. by Sambrook, Fritsch and Maniatis, eds., Cold Spring Harbor Laboratory Press, Chapters 16 and 17; U.S. Pat. No. 4,683,195; DNA Cloning, Volumes I and II, Glover, ed., 1985; Oligonucleotide Synthesis, M. J. Gait, ed., 1984; Nucleic Acid Hybridization, D. Hames & S. J. Higgins, eds., 1984; Transcription and Translation, B. D. Hames & S. J. Higgins, eds., 1984; Culture Of Animal Cells, R. I. Freshney, Alan R. Liss, Inc., 1987; Immobilized Cells And Enzymes, IRL Press, 1986; Perbal (1984), A Practical Guide To Molecular Cloning; See Methods In Enzymology (Academic Press, Inc., N.Y.); Gene Transfer Vectors For Mammalian Cells, J. H. Miller and M. P. Calos, eds., Cold Spring Harbor Laboratory, 1987; Methods In Enzymology, Vols. 154 and 155, Wu et al., eds., Academic Press Inc., N.Y.; Immunochemical Methods In Cell And Molecular Biology (Mayer and Walker, eds., Academic Press, London, 1987; Handbook Of Experimental Immunology, Volumes I-IV, D. M. Weir and C. C. Blackwell, eds., 1986.

The presently-disclosed subject matter is further illustrated by the following specific but non-limiting examples. The following examples may include compilations of data that are representative of data gathered at various times during the course of development and experimentation related to the present invention.

EXAMPLES

Example 1

Formation of Adipose Stromal Vascular Fraction Cell Laden Spheroids Using a 3D Bioprinter and Superhydrophobic Surfaces Materials and Methods.

Fabrication of a Superhydrophobic Surface. The superhydrophobic surface was formed on a polystyrene 48 multiwell plates (Corning, Corning, N.Y.) and 35 mm petri dishes using a 2-step aerosol application of NEVERWET™ (Rust Oleum, Vernon Hills, Ill.). The first step was the application of a binder to the surface as a base coat, which air dried at room temperature for at least one hour. This was followed by the application of a top sheet composed of polydimethylsiloxane modified with hexamethyldisilazane to form the superhydrophobic layer. The superhydrophobic layer thickness was measured to be 0.07 mm. The top sheet subsequently air-dried at room temperature for an additional hour. NEVERWET™ had a reported contact angle of 165° and a surface was considered superhydrophobic beyond contact angles of 150°. The contact angle of both water and unpolymerized collagen in solution was measured via a side view photograph and subsequent contact angle measurement in ImageJ.

Creation of Hydrophilic Spots. Hydrophilic spots on the superhydrophobic surface were created using a 3D bioprinter (Bio-Assembly Tool (BAT) 3-D printer; nScrypt, Inc., Orlando, Fla.) to extrude Pluronic F-127 (Sigma, St. Louis, Mo.). For each hydrophilic spot, the BAT extruded a target volume of 2 µL of 3.8% (wt/wt) Pluronic F-127 in 1× phosphate buffered saline (PBS). With the BAT time-pressure extrusion system, this required 2.5 PSI with an exposure time of 100 ms through a 25G needle to create the appropriate extrusion force to dispense the target volume. These spots were then allowed to air dry for 30 minutes before use.

Stromal Vascular Fraction (SVF) Cells. SVF cells were isolated from rat epididymal fat pads according to previously published enzyme based methods. All animal studies were performed under IACUC (Institutional Animal Care and Use Committee) approval from the University of Louisville, Louisville, Ky. Briefly, fat samples were obtained from rat epididymal fat pads under sterile surgical procedure, minced manually for 3 minutes, washed with PBS that contained 0.1% bovine serum albumin (BSA) and suspended in 2 mg/mL type IV collagenase (Worthington Biochemical Company, Freehold, N.J.). The fat was digested for 35 minutes at 37° C. using an enviro-genie (Scientific Industries, Bohemia, N.Y.). SVF cells were separated from adipocytes by centrifugation (350×g for 4 minutes) after which the supernatant was discarded. The pellet was washed twice with PBS, filtered through a 250 µm filter, and resuspended in endothelial cell media to be used immediately for spheroid bioprinting.

SVF Laden Collagen Spheroid Fabrication. Freshly isolated SVF was suspended in unpolymerized rat tail collagen I mixed with 1× Dulbecco's Modified Eagle Medium (DMEM) (Sigma, St. Louis, Mo.) tittered to a final pH of 7.4 to create a mixture of 3 mg/mL collagen containing $1.6 \times 10^5$ SVF cells mL of final solution. This mixture was kept at 4° C. until printing and a refrigerant system on the bioprinter was used to maintain an equivalent temperature throughout the printing process to prevent gel polymerization. The SVF-collagen solution was transferred to a 3 cc printing syringe (EFD, Nordson, Westlake, Ohio) and placed in a 3D Bioprinter (nScrypt, Inc., Orlando, Fla.). The initial printing conditions were based on previously published data for continuous cylinder printing. Once spheroids were printed they were incubated at 37° C. in a tissue culture incubator (5% $CO_2$) for 10 minutes to initiate collagen gel polymerization.

Spheroid Culture Methods. Following fabrication, spheroids were transferred to a spinner flask (125-mL MagnaFlex Microcarrier Spinner Flask, Wheaton Industries, Millville, N.J.) for cell suspension culture containing endothelial cell growth media composed of DMEM, 10% FBS, 5 mM HEPES buffer, 2 mM L-glutamine, endothelial growth supplement containing heparin, penicillin (45 U/mL), and streptomycin (45 μg/mL). The spinner flask was placed onto a magnetic stirrer platform (MCS 104-L Biological Stirrer, Techne Inc., Burlington, N.J.) to provide continuous suspension of the spheroids, and the magnetic impeller speed was set to 40 rpm throughout the culture period (14 days). Spheroids required for analysis were removed via a 50 mL serological pipette. For spheroid contraction studies, individual spheroids were plated in separate wells of a 96-well ultra-low attachment plate (Corning, Corning, N.Y.).

Spheroid Size Measurements. Spheroid size measurements were calculated from images obtained via light microscopy (CKX41, Olympus, Tokyo, Japan) of spheroids cultured in 96-well plates. Diameter measurements of these 4× images were obtained using ImageJ software.

Live Dead Assay. SVF viability was assessed using live/dead fluorescent stains (Live/Dead Viability/Toxicity Kit, Life Technologies Inc., Carlsbad, Calif.). Spheroids were washed with PBS, incubated with 10 μM calcein AM (live) and 10 μM ethidium homodimer-1 (dead) at room temperature for 45 minutes and imaged via epifluorescent microscopy (IX71, Olympus, Tokyo, Japan). Images were captured at 4× magnification. To quantify the viability of cells in the spheroids produced, SVF cells were isolated and viability was measured using a Nucleocounter and used to create live and dead standard curves. Based on the developed standard curves, viability was measured on days 0, 2, 6, 9, and 13. To supplement the live/dead kit, the distribution of cells was assessed with a Hoechst 33258 bis-benzimide nuclear stain (Anaspec, Calif.) following 15 minutes of 0.1% Triton-X100 (Sigma, St Louis, Mo.) permeabilization.

Confocal Microscopy. For in vitro vascularization analysis, spheroid samples were imaged using an MPE FluoView1000 confocal microscope utilizing a 10× water immersion objective (Olympus, Tokyo, Japan). Confocal image stacks were reconstructed in AMIRA 3D visualization software (Thermo, Waltham, Mass.) and displayed as a z-axis projection. Prior to imaging, spheroids were fixed with 4% paraformaldehyde for 10 minutes at room temperature, then permeabilized with 0.1% Triton X-100 for 15 minutes at room temperature (Sigma, St Louis, Mo.). Following permeabilization, spheroids were stained with Griffonia Simplicifolia-1 Isolectin 4 conjugated to FITC (GS-1) (Vector Laboratories, Burlingame, Calif.) at a dilution of 1:500. Concomitantly, mouse monoclonal α-smooth muscle actin primary antibody was added at 1:250 (α-SMA) (Santa Cruz Biotechnology, Dallas, Tex.). Spheroids were incubated overnight at 4° C. The following day, spheroids were washed 3 times with PBS and incubated with RedDot nuclear stain (Biotium, Fremont, Calif.) and goat anti-mouse IgG Alexa Fluor 594 secondary antibody (Thermo Fisher, Waltham, Mass.) at 1:200 and 1:1000 dilutions respectively for 2 hrs at room temperature. Samples were subsequently washed with PBS and imaged as aforementioned. Endothelial components were stained green with GS-1 FITC. Perivascular support cells as well as fibroblastic components were stained red with α-SMA conjugated to Alexa Fluor 594, and nuclei were stained with RedDot were artificially colored blue.

Statistical Analysis. One way ANOVA with Dunnet's multiple comparisons post-test was used to determine statistical significance between mean spheroid diameters at day 2 and all other subsequent time points via GraphPad Prism 7 for Windows (GraphPad Software Inc., La Jolla, Calif.).

Results

The 3D bioprinter utilized in these studies was capable of time and pressure regulated extrusion of materials at various viscosities using a range of extrusion pen tips. Measured contact angles for water and a suspension of cells, media, and collagen at printed concentrations were recorded at 155° and 156° respectively. Table I illustrates the range of printing parameters tested. The parameters selected represent the conditions that provided consistent extrusion of spheroids with uniform size at a rate of 10.3 spheroids/min. Syringe pressure, pressure duration, and needle gauge all combine to determine extrusion speed and therefore spheroid size. Higher pressures and larger needle gauges allow for more consistent results and were selected for those reasons. Pressure duration was kept low to maintain spheroid volumes. Cartridge size was selected to best fit the batch volumes and collagen concentration was selected to maintain the spheroid properties compared to unprinted collagen gels. Previously published conditions necessary to extrude cell laden collagen cylinders with maintenance of cell viability were used as a starting point for the current studies.

TABLE I

3D Printing Conditions to Create Spheroids

| Printing Parameter | Selected Value | Range Evaluated |
| --- | --- | --- |
| [a] Syringe Pressure | 5 psi | 3-6 psi |
| [b] Pressure Duration | 100 ms | 100-300 ms |
| [c] BAT Cartridge Size | 3 cc | 3 cc |
| [d] Needle Gauge- Tip Type | 18 g - blunt | 18-25 g blunt |
| [e] Collagen Concentration | 3 mg/ml | 3 mg/ml |

[a] Pressure effects evaluated using 100 ms pressure duration
[b] Time of pressure extrusion evaluated at a constant 5 psi syringe pressure
[c] The nScrypt Bioassembty Tool utilizes EFD cartridges in a precision fluid dispensing system (Nordson Corporation, Westlake OH).
[d] Nordson EFD extrusion tips
[e] Rat tail derived collagen.

Figure 1B:
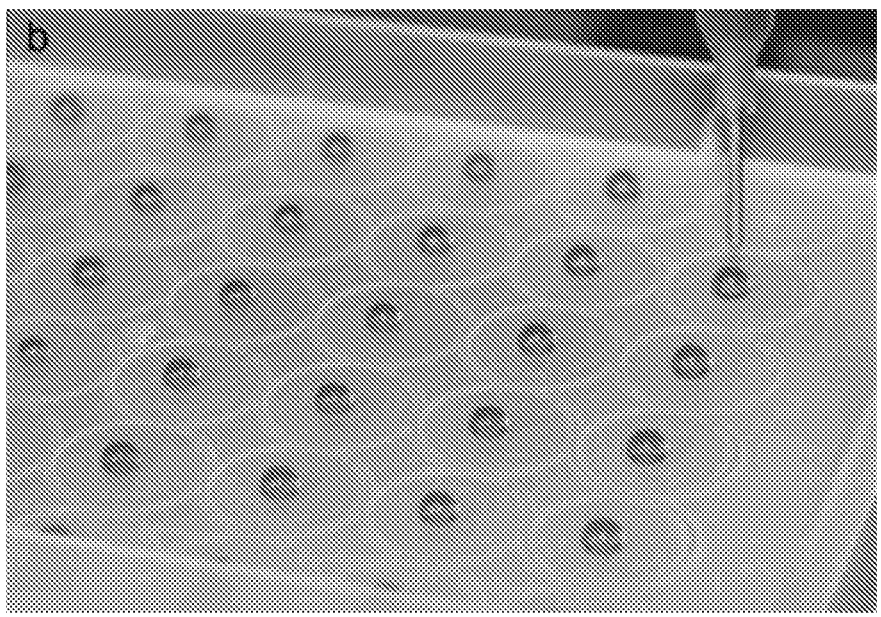
Figure 1C:
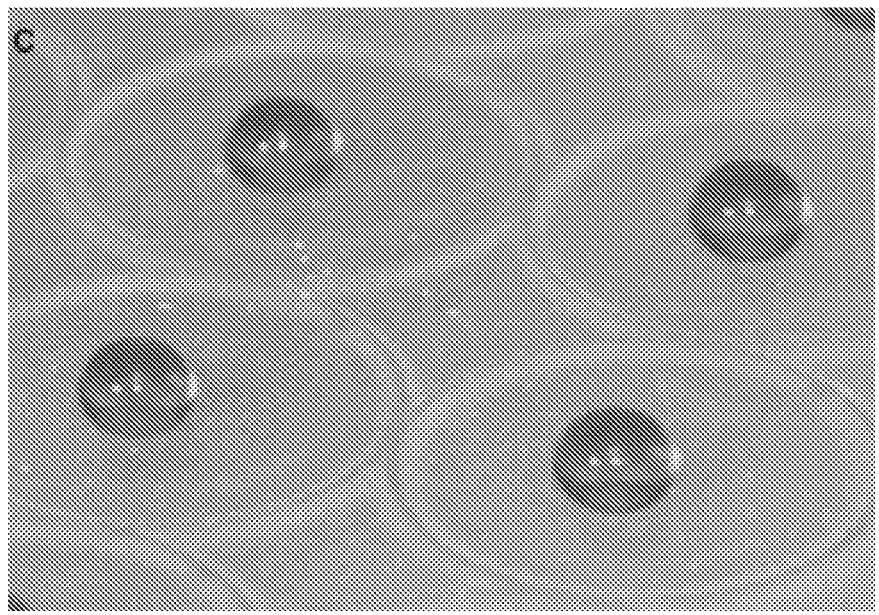
Figure 1D:
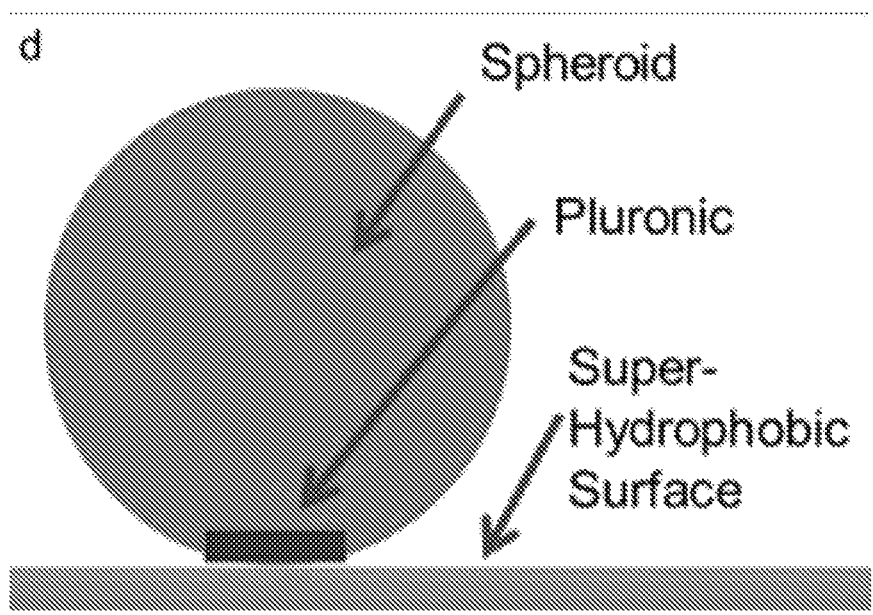

To maintain spheroid morphology after collagen extrusion but before collagen polymerization, a superhydrophobic coating was utilized on tissue culture polystyrene plates and 3D spheroids were bioprinted directly onto those surfaces. As illustrated in FIGS. 1A-1B, the spheroids were immobilized on the super-hydrophobic surface by Pluronic® F127 throughout stage movement (X-Y axes) during printing and subsequent transport to an incubator for gelation. That Pluronic® F127 disk on the superhydrophobic surface is illustrated in the diagram in FIG. 1D. Spheroids could then be easily released from the Pluronic® F127 either by incubation in an aqueous solution or by cooling the surface to 10° C. Throughout the entire process, the spheroids maintained their shape on those superhydrophobic surfaces as well as after removal.

Batches of spheroids were prepared using 2 mL of unpolymerized collagen I containing suspended SVF cells, and were produced in quantities of 100 to 150 spheroids per batch depending upon size. Spheroids had a mean diameter of 3.54 mm with a standard deviation of 0.195 mm. Batch production time required 20 minutes of instrument preparation and 5 minutes per 48 spheroids extruded. After extrusion, the spheroids were incubated for 10 minutes at 37° C. resulting in a total production time of 30-35 minutes before spheroid usage.

Figure 2A:
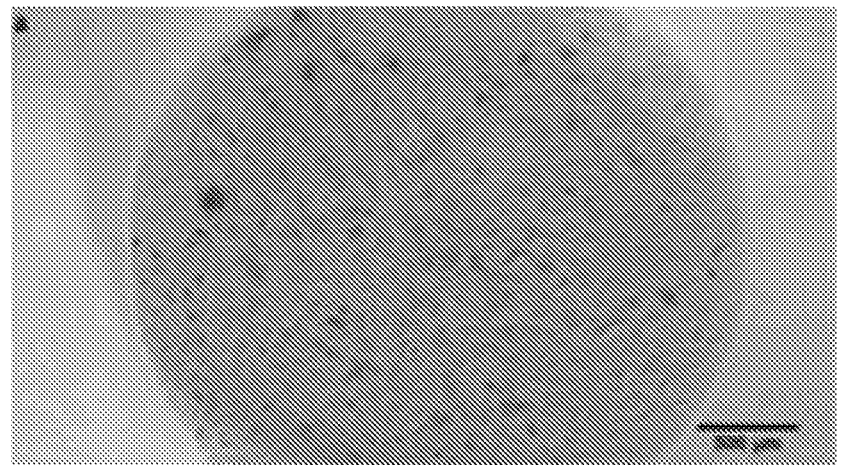
FIG. 2A-2H includes images showing: spheroid morphology as visualized by phase contrast microscopy (FIGS. 2A and 2E); encapsulated SVF morphology as visualized by epifluorescence at 4× magnification for live cells (FIGS. 2B and 2F), dead cells (FIGS. 2C and 2G); and cellular distribution (FIGS. 2D and 2H) as visualized using calcein AM, ethidium homodimer-1, and Hoechst 33258 bis-benzimide respectively. Spheroids were cultured for 2 days (FIGS. 2A-2D) and for 6 days (FIGS. 2E-2H) in spinner culture. The micrograph shown in FIG. 2H was obtained from a different spheroid than those shown in FIGS. 2E-2G.
Figure 2B:
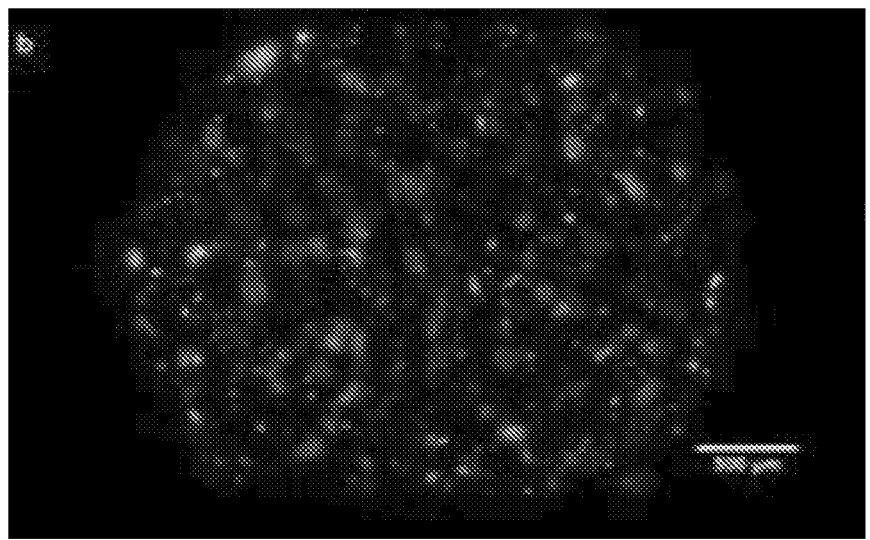
Figure 2C:
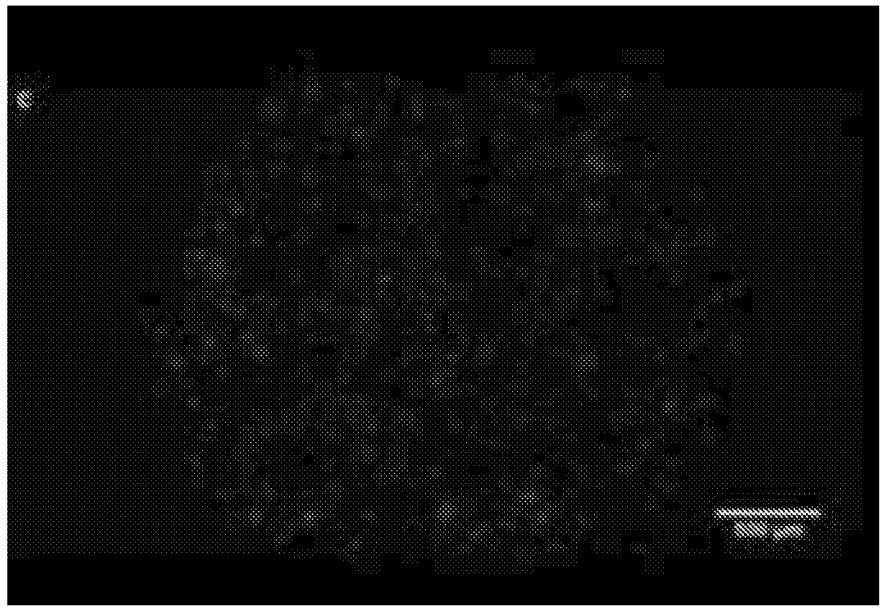
Figure 2D:
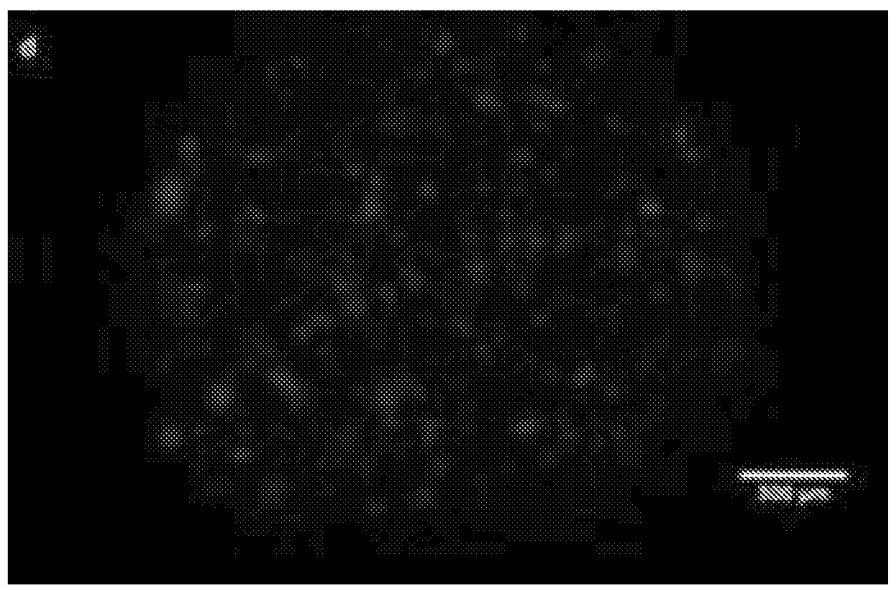
Figure 2E:
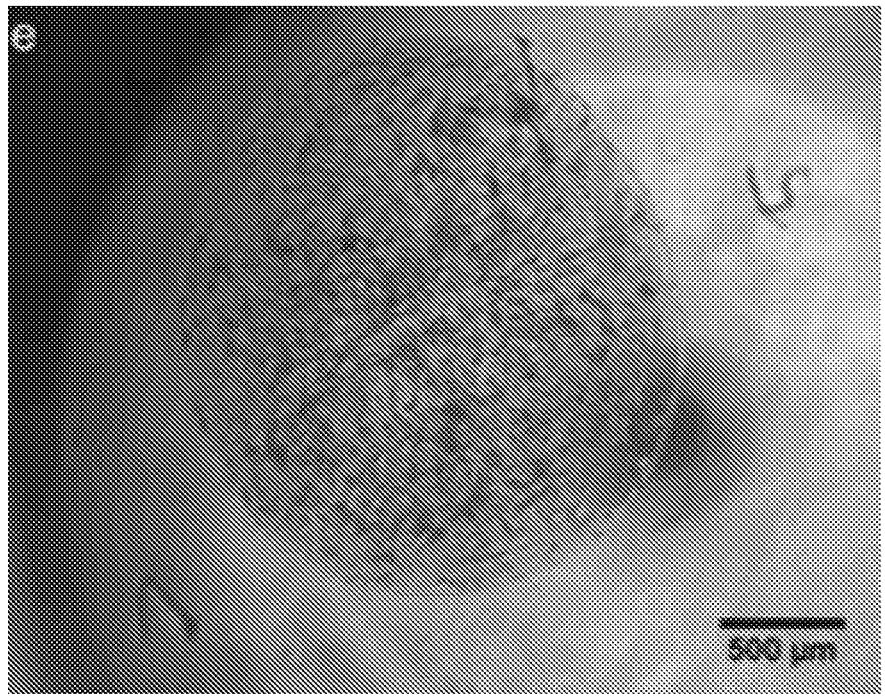
Figure 2F:
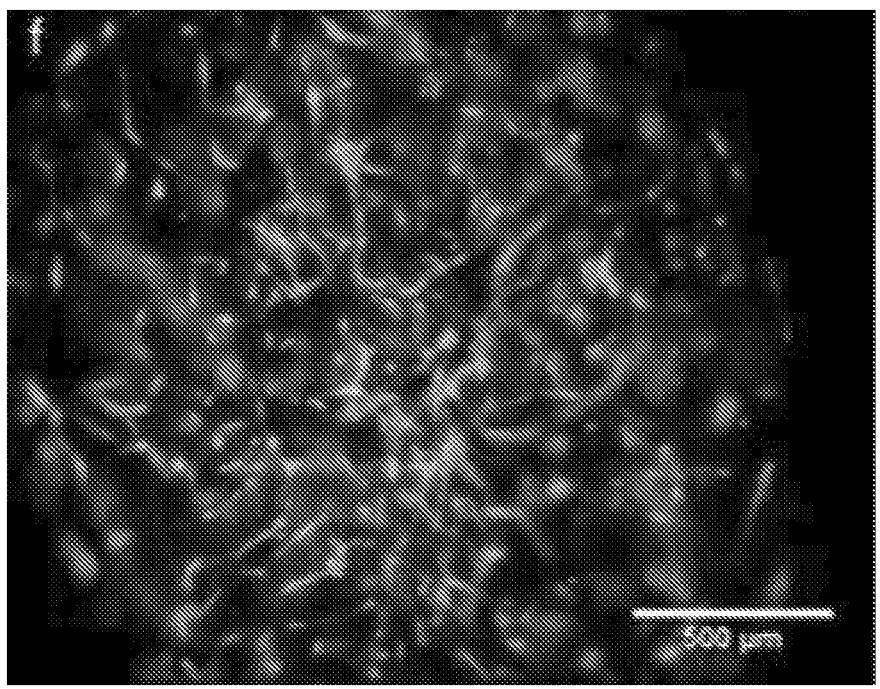
Figure 2G:
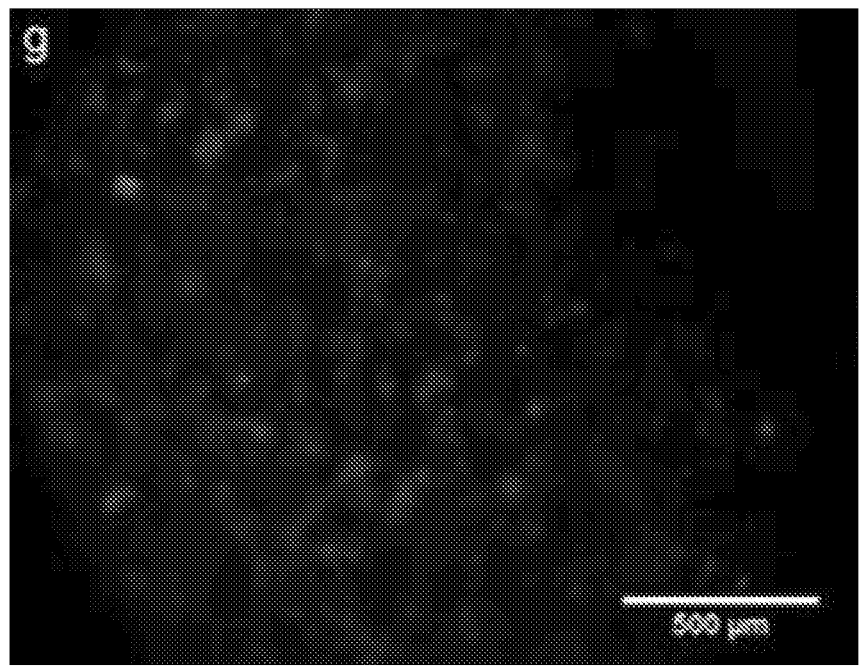
Figure 2H:
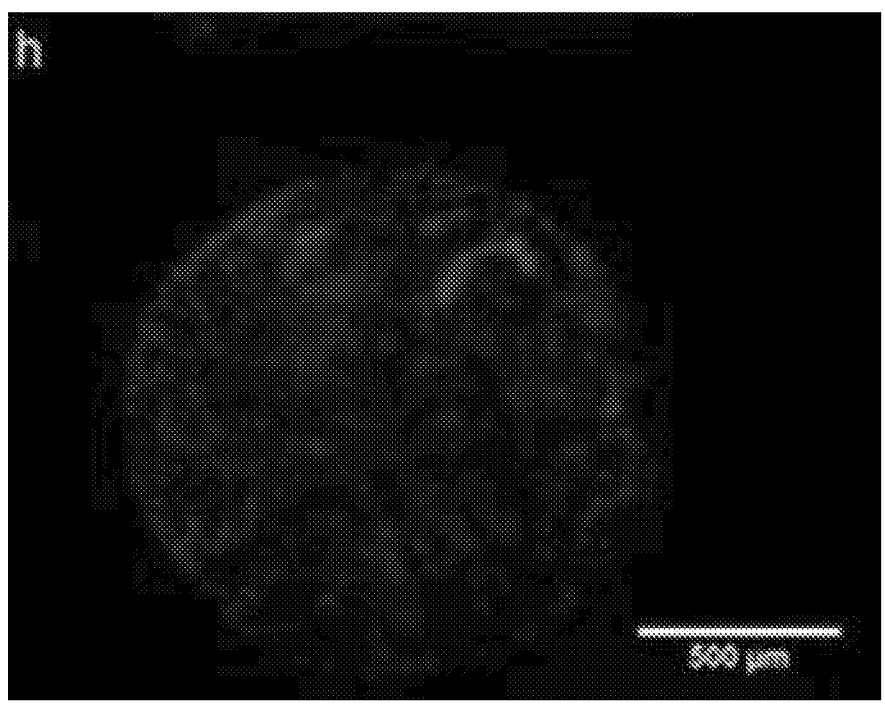

The typical morphology of 3D Bioprinted SVF spheroids after initial collagen gelation is shown in FIGS. 2A-2H. The SVF laden spheroid morphology, visualized by phase contrast microscopy was uniform (FIG. 2A), and the engrafted cells were mostly viable as demonstrated by calcein AM live stain (FIG. 2B). A few non-viable cells, labelled with ethidium homodimer-1 were present as seen in FIG. 2C. The distribution of cells assessed by nuclear staining with bis-benzimide (FIG. 2D) was homogeneous indicating the gelation of collagen maintains cell encapsulation throughout the spheroid with no evidence of cell settling within a particular location. The distribution and viability of the cells within the spheroids were assessed again after 6 days in spinner culture. Live cells (calcein AM positive) are seen in FIG. 2F, with dead cells (ethidium homodimer-1 positive) shown in FIG. 2G, and total cell distribution by nuclear staining (bis-benzimide positive) shown in FIG. 2H. At this culture time point, morphological changes in the encapsulated SVF were noted including microvessel structures with elongated sprouts and complex geometries suggesting the occurrence of in vitro angiogenesis in 3D collagen I.

Figure 3:
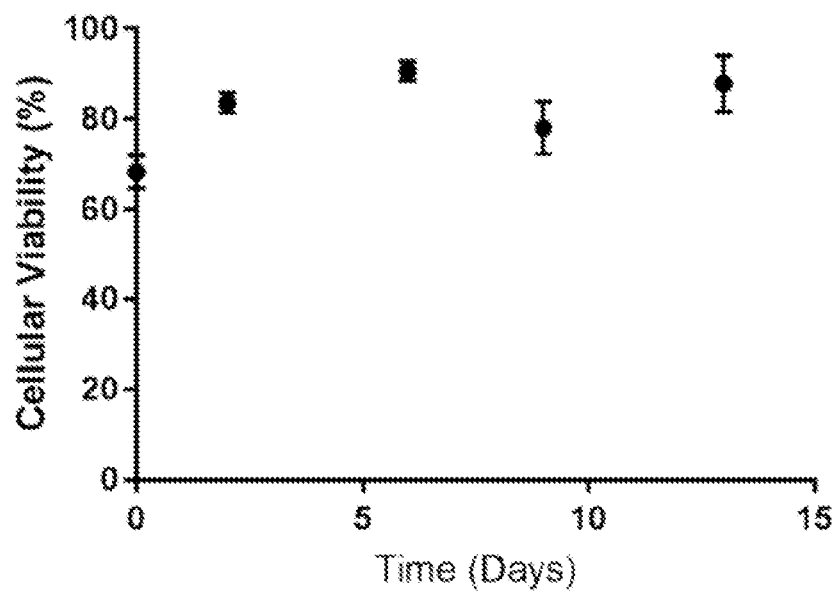
FIG. 3 is a graph showing cell viability within spheroids on days 0, 2, 6, 9, and 13.
Figure 4A:
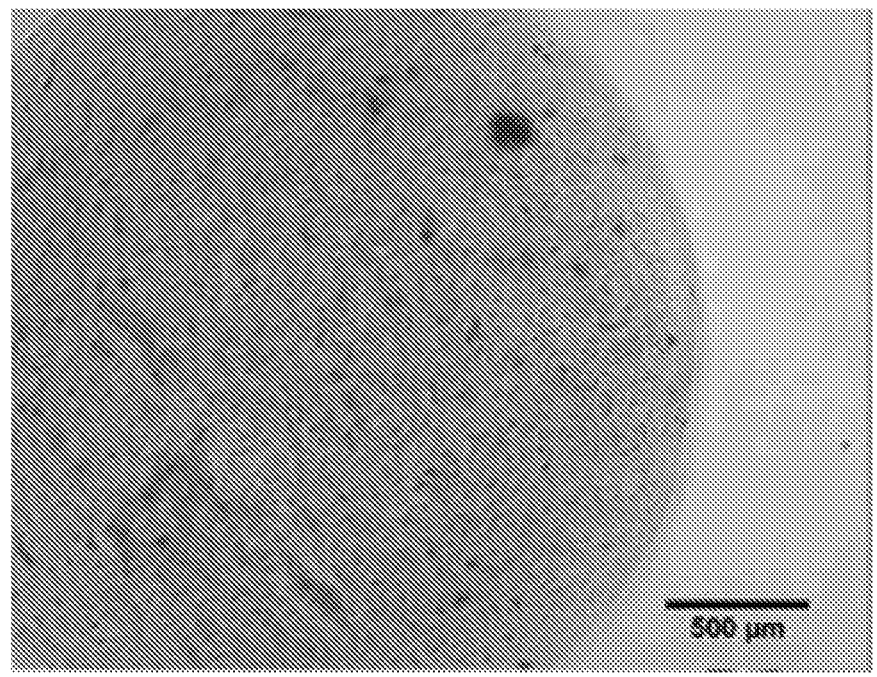
FIGS. 4A-4D include images showing 4× magnification phase contrast micrographs of an SVF laden collagen I spheroid on days 2 (FIG. 4A), 6 (FIG. 4B), 9 (FIG. 4C), and 13 (FIG. 4D) of spinner culture.
Figure 4B:
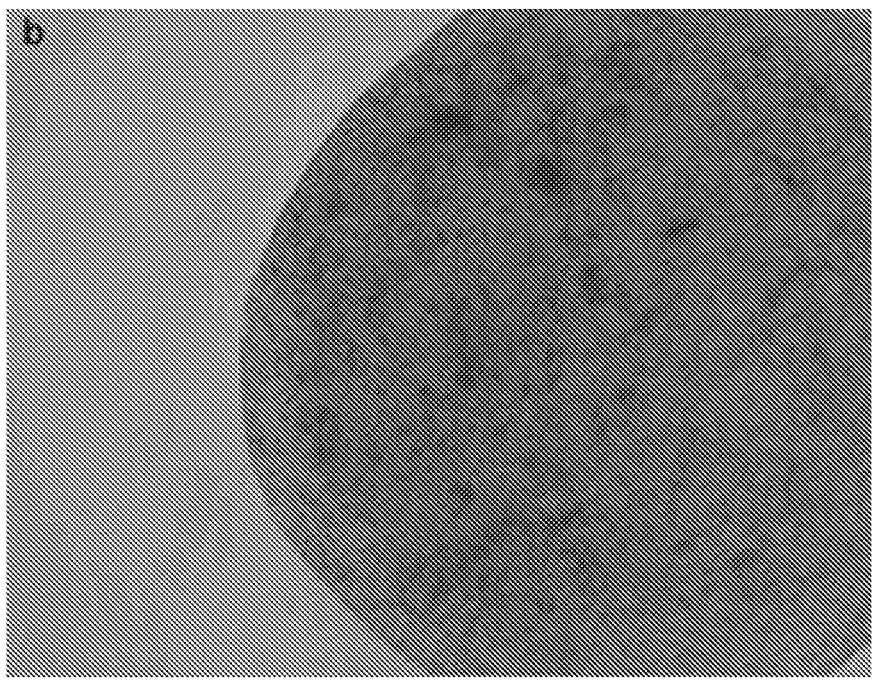
Figure 4C:
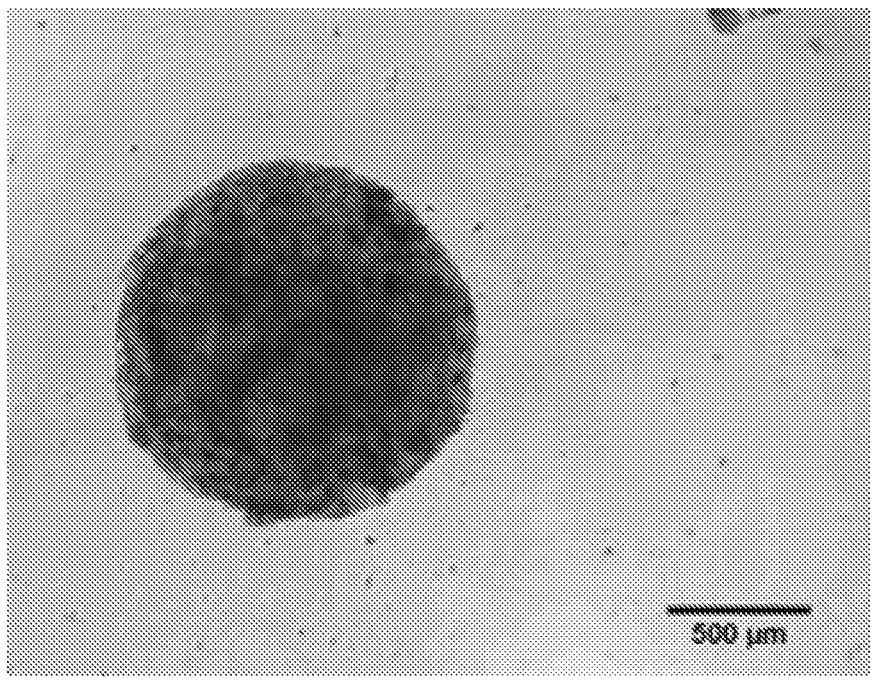
Figure 4D:
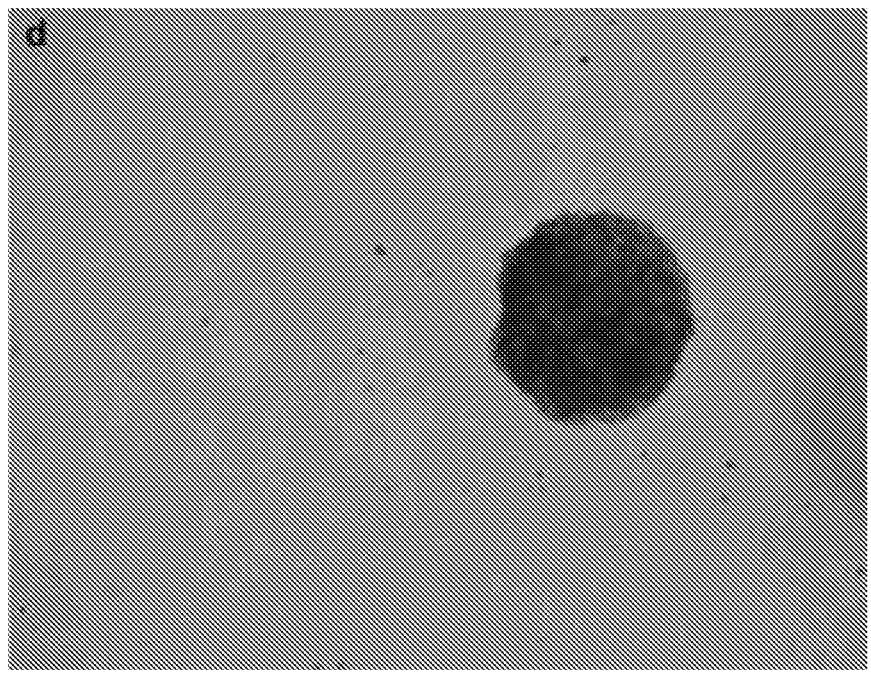

SVF viability was quantified immediately after printing on day 0 and throughout the culture period on days 2, 6, 9, and 13 in FIG. 3. Day 0 printed viability (68.24%±3.59%) was on average 5.96% lower than that of pipetted encapsulation controls and 27.8% lower than Nucleocounter based viability before encapsulation.

Figure 5:
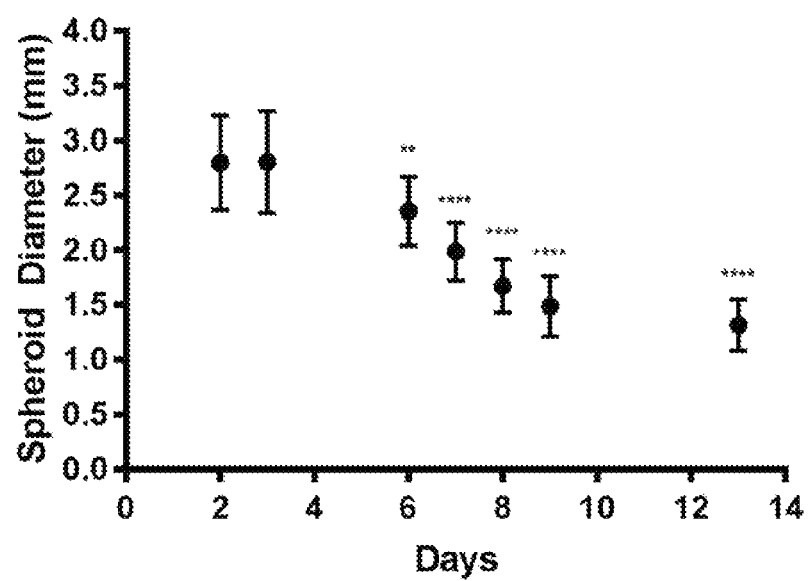
FIG. 5 is a graph showing SVF laden collagen spheroids undergo a significant mean diameter decrease from 6 to 13 days of spinner culture incubation (n=12). Statistical significance determined at $P<0.05$. $P<0.01$, $**P<0.0001$.

Studies of the spheroids during suspension culture indicated the spheroids undergo contraction with concomitant reduction in diameter. The contraction of the spheroids is illustrated by phase contrast microscopy in FIGS. 4A-4D and was quantitatively assessed with results provided in FIG. 5. Early collagen contraction occurred at an average rate of 0.0083±0.0875 mm/day from days 2-3 and the rate of contraction increased to its peak rate of 0.3675±0.1359 mm/day from days 6-7 days in spinner culture. Following that peak, contraction rate decreased to 0.042±0.0463 mm/day from days 9-13 in spinner culture. Average spheroid diameters were significantly different between days 2 and all subsequent days in culture (FIG. 5, $p<0.0001$).

Figure 6A:
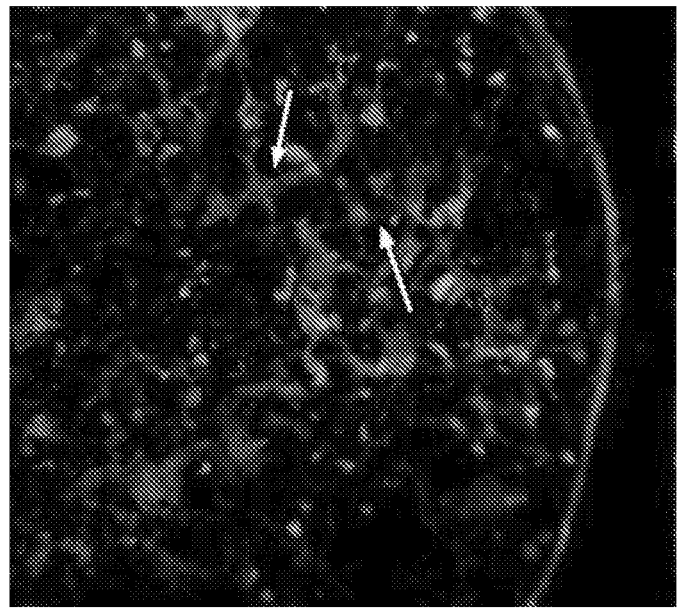
FIGS. 6A-6B includes images showing 10× magnification confocal micrographs of a SVF laden collagen I spheroid after 14 days in spinner culture and stained with the endothelial specific lectin Griffonia simplicifoli, GS-1 (green), alpha smooth muscle cell actin, ($\alpha$-SMA) (red), and nuclear stain, RedDot (blue). Tube like structures are highlighted with arrows.
Figure 6B:
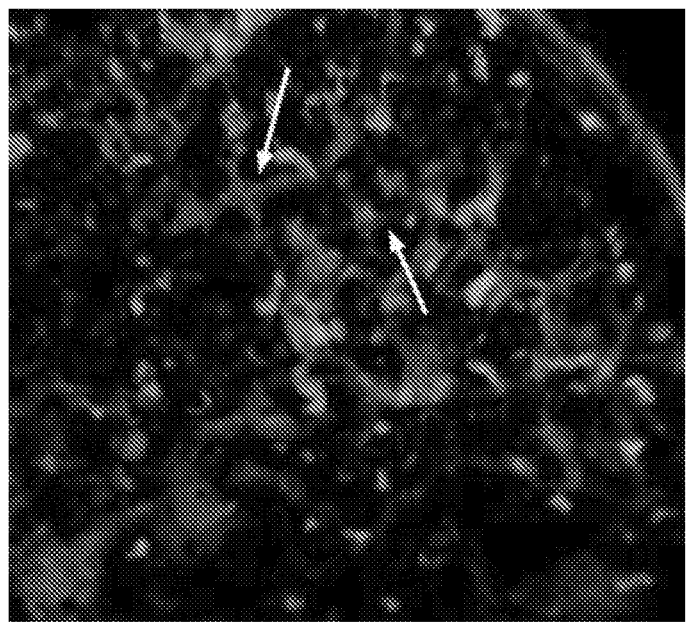

The general morphology of the SVF spheroids was assessed after 14 days in spinner culture, a time point where spheroids have undergone significant contraction. Due to the high density of cells in contracted spheroids, epifluorescence was inadequate to produce clear images of cellular morphology. As such, to accurately visualize the distribution of cells and to characterize vascular cell phenotype in contracted spheroids, 14 day spheroids were stained for endothelial (GS-1 FITC positive) and α-smooth muscle actin (α-SMA-Alexa Fluor 594 positive) components and evaluated by confocal microscopy. Amira software was subsequently used to create 3D volume renderings of the entire construct. Cells not only retained viability over time in culture, they also underwent phenotypic changes towards vessel-like structures as seen before in 3D collagen I in vitro assays utilizing SVF. An example of cellular components exhibiting tube-like formation with the presence of endothelial cells abluminally surrounded by αSMA positive cells adventitially, provides evidence of angiogenesis in vitro, and is highlighted by arrows in FIGS. 6A-6B.

Discussion

The delivery of stem and regenerative cells, including stromal vascular fraction, for the treatment of various diseases has reached human clinical trials; however, the limited retention of cells at the site of implantation has been implicated in observed poor therapeutic effect. Alternative methods to improve retention have included the self-aggregation of cells in culture and the encapsulation of cells within a biomaterial. These studies have established an improvement in cell retention at the site of implantation. Stromal vascular fraction has been encapsulated in a variety of materials to improve cell retention including alginate, to create SVF containing spheroids. Retention of SVF in alginate maintains cell viability; however, alginate gels do not show any morphological change which implies that they do not support engrafted cell migration and proliferation, thus limiting in vitro angiogenesis and potential in vivo application for cell-based therapies. For this reason, the use of collagen type I was explored for spheroid production as SVF cell populations have been shown to exhibit in vitro angiogenesis within that extracellular matrix. SVF laden collagen gels can be created in sheets and are cumbersome to manipulate. Additionally, collagen spheroids printed onto conventional tissue plates rapidly flatten due to the hydrophilic characteristics of polystyrene. In order to maintain collagen I in a spheroid shape after extrusion and after polymerization, a superhydrophobic coating was utilized on tissue culture polystyrene plates and 3D bioprinted directly onto these surfaces.

Initial attempts to print onto superhydrophobic surfaces were unsuccessful at first due to the inability of spheroids to attach to the superhydrophobic surface, with most remaining attached to the printing pen tips. To overcome this lack of adherence, a disk of Pluronic F-127 was printed onto the superhydrophobic surface. Pluronic F-127 is a triblock co-polymer with an amphiphilic block structure which gives it hydrophilic and hydrophobic properties. This allows Pluronic F-127 to both adhere to the superhydrophobic surface and adhere to an aqueous material such as collagen. With the biphilic surface established, collagen spheroids were produced using conditions that provided a variety of sizes. Mean diameter adjustments could be made via changes in applied pressure which allowed the production of spheroids ranging in size from 1 mm to 3.5 mm.

In comparison to self-assembly based spheroid production methods, biphilic spheroid production is an order of magnitude faster with similar consistency in spheroid size and shape. The primary source of spheroid size variation when using an automated time-pressure extrusion system such as the BAT is the viscosity of the fluid being dispensed. However, all parameters including stable neutral pH, low temperature, and thorough mixing of the unpolymerized collagen solution before BAT extrusion were addressed to minimize variation within a spheroid batch.

These studies indicate that spheroid integrity and cell distribution are maintained throughout the 14 day cell culture period either in static culture or in more dynamic spinner culture conditions. The viability of the cells measured by the Nucleocounter before encapsulation in collagen was 96% so the day 0 viability dropped by just under 30% during the process of collagen embedding. However, the viability within pipetted collagen was only 5.96% higher than that of the printed collagen which leads to the conclusion the collagen encapsulation rather than the bioprinting is the source of the viability decrease. This conclusion is in conflict with the prior research into the viability within pipetted collagen carried out by other showing >90% viability for pipetted collagen and printed collagen. Especially given that others used the same markers for their viability assays with cells of the same origin encapsulated in collagen of the same concentration. The two differences that most likely contribute to the viability difference seen are that others cultured their cells before printing as opposed to the present use of fresh isolate and the present use of rat tail collagen while their collagen source was not listed. This conflict could be attributed to the fact that others did their cell counts for viability by eye rather than by fluorescence values. Counting cells for viability by eye leaves the data vulnerable to user bias against dimmer objects. This issue is potentially exaggerated by the fact that in terms of relative fluorescence units (RFU), the live cells are an order of magnitude brighter than an equivalent number of dead cells and brightness compensation for image based viability counts is frequently unregulated. This seems especially likely given that others clarified that the cells had to be stained brightly in either color to be counted. This was further supported by the fact that the difference in viability between pipetted and printed cells is similar for both studies. A potential issue with fluorimeter based viability is the possibility of non-specific staining skewing results; however, the present use of stained acellular collagen spheroids as baselines should have helped compensate for acellular signals and the standard curve should compensate for cellular non-specific staining. Following day 0, viability remained high throughout the duration of the spinner culture although there was a drop in viability that coincided with later stage spheroid contraction at day 9.

In contrast to results using alginate to form spheroids, there was a noticeable change in cell morphology that demonstrated the ability of cells to undergo initial steps of angiogenesis including, but not limited to, tip cell formation and sprouting from retained microvessel fragments. Contraction of the SVF-collagen spheroids was also observed commencing after 6 days of cell culture. Collagen contraction in the presence of fibroblasts and endothelial cells has been well documented and it has been suggested that cell-dependent contraction provides an assessment of active metabolism, microenvironment remodeling, and cellular motility of these embedded cells. Confocal microscopic analysis of cellular composition and phenotype in contracted spheroids suggested the presence of organized, elongated, tube structures that stain positive for the endothelial cell specific lectin Griffonia simplificiolia-1 (GS-1) in conjunction with α-smooth muscle actin. This phenotypic change over time provided evidence that SVF was either self-organizing into microvessel-like structures (vasculogenesis) or endothelial cells were sprouting from pre-existing microvessel fragments (angiogenesis). Angiogenesis and neovascularization of SVF in vitro provides therapeutic potential to utilize pre-vascularized collagen I spheroids for the treatment of ischemic conditions in vivo.

Automation through direct write computer assisted design and manufacturing provided the opportunity to produce spheroids in a controlled, precise, and efficient manner utilizing biphilic surfaces. Such systems also presented the opportunity to design high throughput microenvironment-based assays for a plethora of purposes including drug delivery, cell delivery, or immunotherapy delivery. A number of in vitro applications of spheroids have yet to be investigated. The ability to produce a multitude of extracellular matrix-based spheroids composed of biomaterials such as fibrin, hyaluronic acid, and other unexplored hydrogels would allow the creation of microenvironments suitable for a variety of cell-based therapies. Indeed, phenotypic variation and cellular function may be different depending upon the ECM used. In vivo studies are also necessary to address and characterize the therapeutic benefit of encapsulated cells, including functional interaction with surrounding host tissue, in comparison to direct injection of liquid suspended cells alone.

In summary, the foregoing study demonstrated that a biphilic surface can be used to create viable SVF laden spheroids of uniform size and shape. The addition of automation via a 3D bioprinter allows for high throughput and a production time low enough to fit within a point of care clinical setting. Further, the use of a water soluble hydrophilic spot and the phase transition properties of Pluronic F-127 allow for minimally disruptive spheroid removal for any applications that would require spheroid manipulation. These SVF laden collagen spheroids can offer a strategy to increase the therapeutic effect of cellular infusions for regenerative purposes via improved cellular localization and retention.

Example 2

Production of Islet Cell-Laden Spheroids

Methods

Fabrication of a Superhydrophobic Surface, Creation of Hydrophilic Spot, and Isolation of SVF Cells. The fabrication of the superhydrophobic surface and the creation of the hydrophilic spot was performed substantially as described above in Example 1. SVF cells were again isolated from rat epididymal fat pads according to previously published enzyme based methods as also described above in Example 1.

Islet Isolation. Islets were isolated according to the methods of Balamarughan.

Islet/SVF Laden Collagen Spheroid Fabrication. Freshly isolated SVF and islets were suspended in unpolymerized rat tail collagen I mixed with 1× Dulbecco's Modified Eagle Medium (DMEM) (Sigma, St. Louis, Mo.) tittered to a final pH of 7.4 to create a mixture of 3 mg/mL collagen containing $1.6 \times 10^5$ SVF cells/mL of final solution. This mixture was kept at 4° C. until printing and a refrigerant system on the bioprinter was used to maintain an equivalent temperature throughout the printing process to prevent gel polymerization. The Islet/SVF-collagen solution was transferred to a 3 cc printing syringe (EFD, Nordson, Westlake, Ohio) and placed in a 3D Bioprinter (nScrypt, Inc., Orlando, Fla.). The initial printing conditions were based on our previously published data for continuous cylinder printing [4, 5, 31, 42]. Once spheroids were printed they were incubated at 37° C. in a tissue culture incubator (5% $CO_2$) for 10 minutes to initiate collagen gel polymerization.

Spheroid Culture Methods. Following fabrication, spheroids were transferred to a spinner flask (125-mL MagnaFlex Microcarrier Spinner Flask, Wheaton Industries, Millville, N.J.) for cell suspension culture containing endothelial cell growth media [85] composed of DMEM, 10% FBS, 5 mM HEPES buffer, 2 mM L-glutamine, endothelial growth supplement containing heparin, penicillin (45 U/mL), and streptomycin (45 µg/mL). The spinner flask was placed onto a magnetic stirrer platform (MCS 104-L Biological Stirrer, Techne Inc., Burlington, N.J.) to provide continuous suspension of the spheroids, and the magnetic impeller speed was set to 40 rpm throughout the culture period (14 days). Spheroids required for analysis were removed via a 50 mL serological pipette. For spheroid contraction studies, individual spheroids were plated in separate wells of a 96 well ultra-low attachment plate (Corning, Corning, N.Y.).

Spheroid Size Measurements. Spheroid size measurements were calculated from images obtained via light microscopy (CKX41, Olympus, Tokyo, Japan) of spheroids cultured in 96 well plates. Diameter measurements of these 4× images were obtained using ImageJ software.

Live Dead Assay. Islet and SVF viability was assessed using live/dead fluorescent stains (Live/Dead Viability/Toxicity Kit, Life Technologies Inc., Carlsbad, Calif.). Spheroids were washed with PBS, incubated with 10 µM calcein AM (live) and 10 µm ethidium homodimer-1 (dead) at room temperature for 45 minutes and imaged via epifluorescent microscopy (IX71, Olympus, Tokyo, Japan). Images were captured at 4× magnification. In order to quantitatively evaluate the viability of the spheroids produced, SVF cells were isolated and viability was measured using a Nucleocounter and used to calculate known amounts of live and dead cells. From there, known amounts of cells were pipetted, stained, and analyzed with a fluorimeter in order to obtain live and dead fluorescence values for the respective cell quantities. The standard curves developed from these values are shown below (n=3). Based on the developed standard curves, viability was measured on days 0, 2, 6, 9, and 13. To supplement the live/dead kit, the distribution of cells was assessed with a Hoechst 33258 bis-benzimide nuclear stain (Anaspec, Calif.) following 15 minutes of 0.1% Triton-X100 (Sigma, St Louis, Mo.) permeabilization.

Insulin release. Insulin release was quantified using ELISA

Prevascularized Islet Implant Studies. Prevascularized islets were implanted into immunocompromised mice made diabetic by infusion of streptozotocin. The prevascularized islets were implanted subcutaneously. Blood glucose levels were measured post islet transplantation.

Confocal Microscopy. For in vitro vascularization analysis, spheroid samples were imaged using an MPE FluoView1000 confocal microscope utilizing a 10× water immersion objective (Olympus, Tokyo, Japan). Confocal image stacks were reconstructed in AMIRA 3D visualization software (Thermo, Waltham, Mass.) and displayed as a z-axis projection. Prior to imaging, spheroids were fixed with 4% paraformaldehyde for 10 minutes at room temperature, then permeabilized with 0.1% Triton X-100 for 15 minutes at room temperature (Sigma, St Louis, Mo.). Following permeabilization, spheroids were stained with Griffonia Simplicifolia-1 Isolectin 4 conjugated to FITC (GS-1) (Vector Laboratories, Burlingame, Calif.) at a dilution of 1:500. Concomitantly, mouse monoclonal α-smooth muscle actin primary antibody was added at 1:250 (α-SMA) (Santa Cruz Biotechnology, Dallas, Tex,). Spheroids were incubated overnight at 4° C. The following day, spheroids were washed 3 times with PBS and incubated with RedDot nuclear stain (Biotium, Fremont, Calif.) and goat anti-mouse IgG Alexa Fluor 594 secondary antibody (Thermo Fisher, Waltham, Mass.) at 1:200 and 1:1000 dilutions respectively for 2 hrs at room temperature. Samples were subsequently washed with PBS and imaged as aforementioned. Endothelial components were stained green with GS-1 FITC. Perivascular support cells as well as fibroblastic components were stained red with α-SMA conjugated to Alexa Fluor 594, and nuclei were stained with RedDot were artificially colored blue.

Statistical Analysis. One way ANOVA with Dunnet's multiple comparisons post-test was used to determine statistical significance between mean spheroid diameters at day 2 and all other subsequent time points via GraphPad Prism 7 for Windows (GraphPad Software Inc., La Jolla, Calif.).

Results and Discussion

Figure 7A:
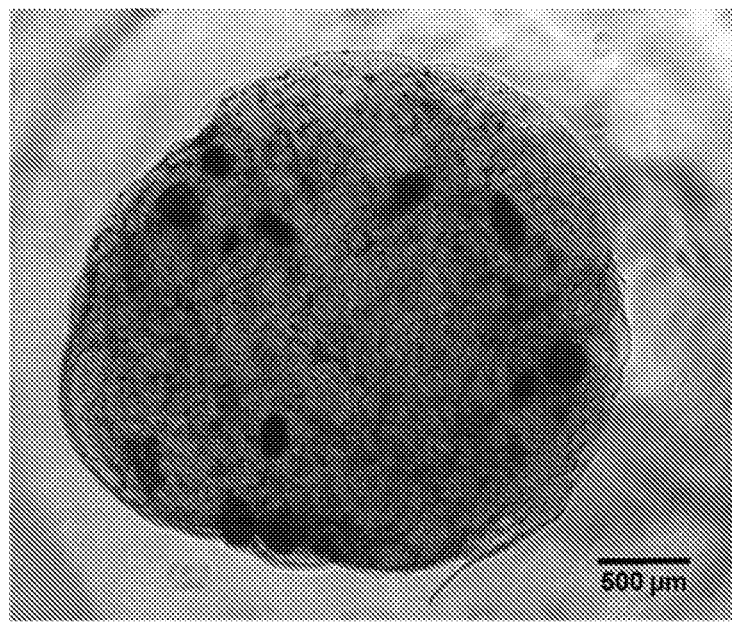
FIGS. 7A-7B are includes images showing a bioprinted human adipose SVF/Islet spheroid illustrating the feasibility to create a prevascularized islet implant using a 3D bioprinting system, and a superhydrophobic surface.
Figure 7B:
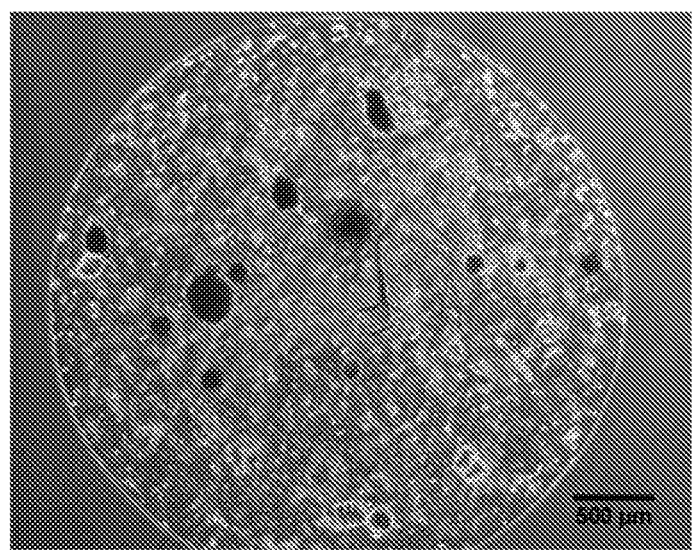
Figure 8:
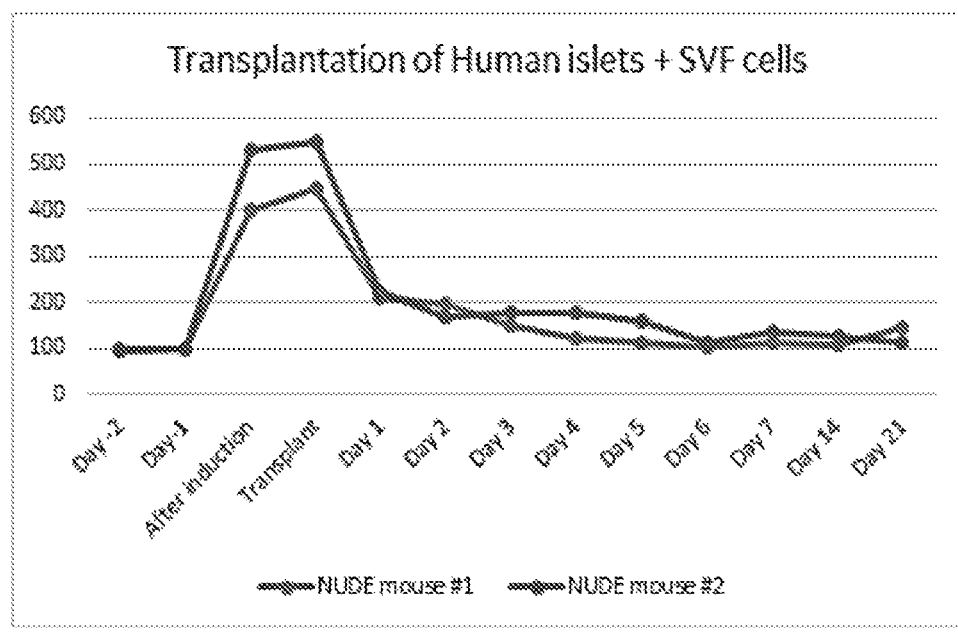
FIG. 8 is a graph showing the ability of islet/SVF spheroids to correct hyperglycemia in a diabetic animal model.
Figure 9A:
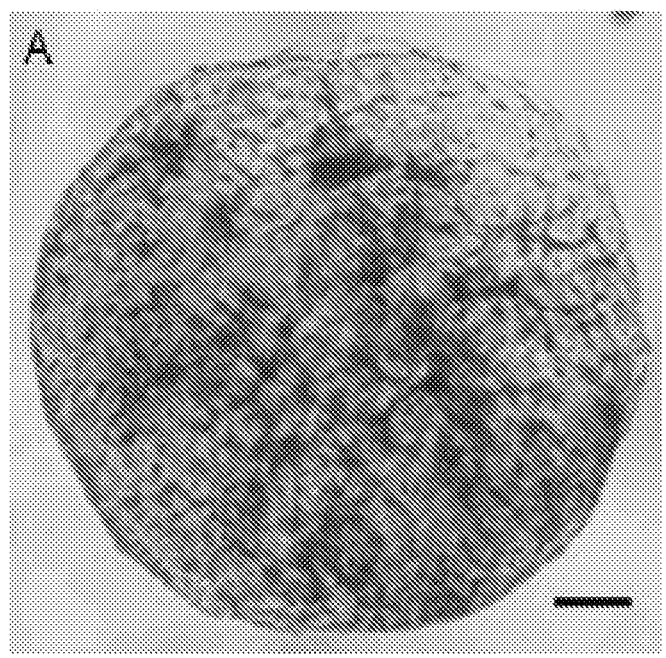
FIGS. 9A-9G include phase contrast and confocal microscopy images of SVF spheroids.
Figure 9B:
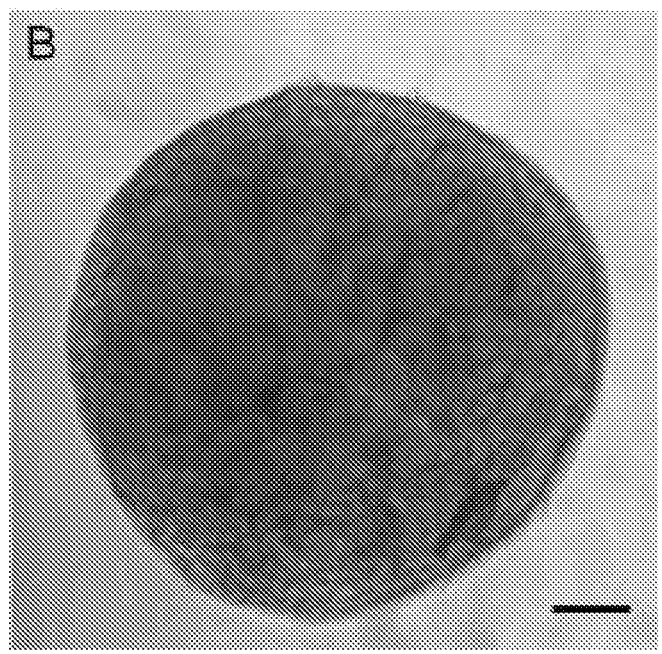
Figure 9C:
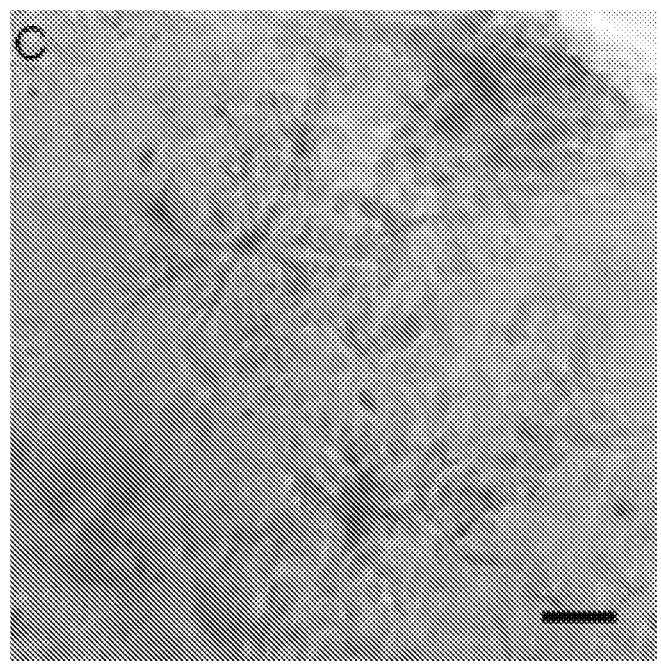
Figure 9D:
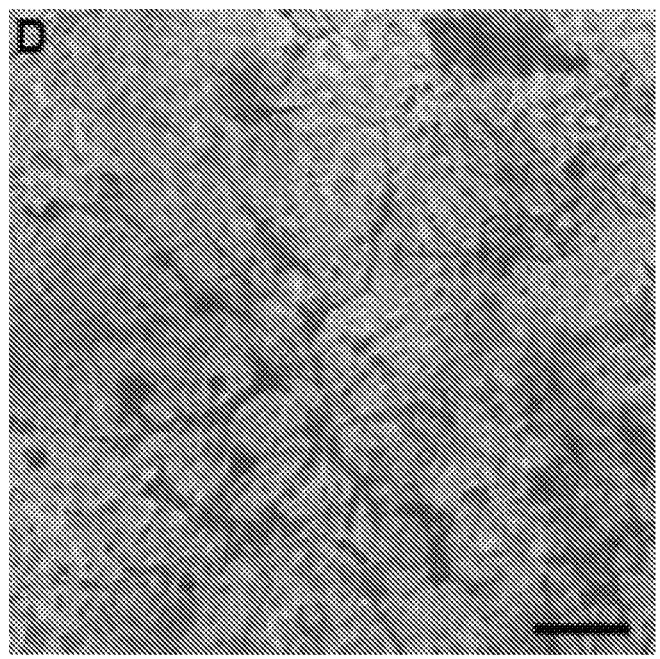
Figure 9E:
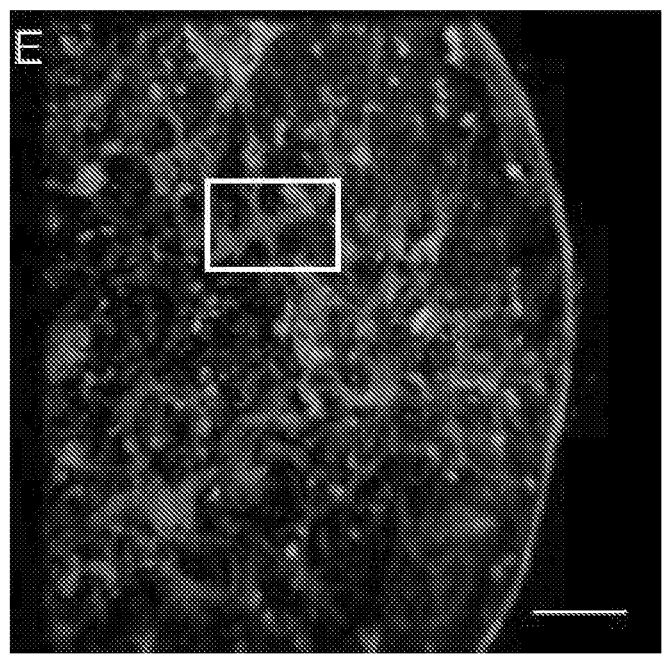
Figure 9F:
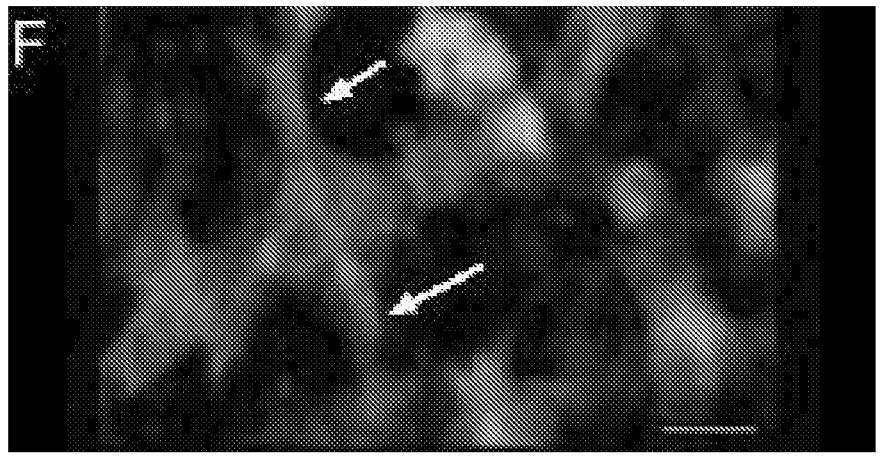
Figure 9G:
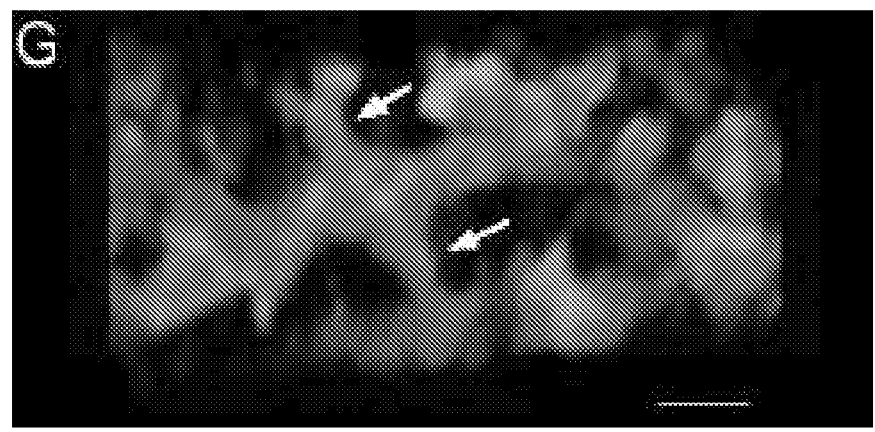

Three-dimensional bioprinting represents a novel approach to the development of tissue constructs for implantation. The present studies have been completed to show the feasibility of printing adipose derived SVF cells and adipose derived microvascular fragments and subsequently implanting these constructs to evaluate their viability and retention. A further enabling technology has been developed for the bioprinting of islet constructs utilizing a technique to create cell encapsulated spheroids of defined size. The first studies utilized alginate as an encapsulating biomaterial. While these studies established the ability to co-localize adipose SVF and islets, and the islets remained viable for up to 14 days in culture, a lack of host vessel integration with the spheroid circulation was observed. Accordingly, alternative methods were explored to create spheroids with a focus on the use of collagen type 1 as a matrix molecule. As described above, a technological solution was found using superhydrophobic and hydrophilic surfaces to maintain the spheroid shape of non-viscous solutions In this regard, and similar to what is shown in FIG. 1, a bioprinting system was used to bioprint spheroids containing islets and adipose SVF. FIG. 7 is an image of such spheroids and evidences the ability to co-print islets and adipose-derived regenerative cells. FIG. 7 illustrates the cellular distribution in these spheroids and the ability to print and maintain structural integrity of islet/SVF spheroids for periods in excess of 7 days in spinner culture. Further, as shown in FIG. 8 and FIGS. 9A-9G, studies have established the ability to correct hyperglycemia in a diabetic animal model and have shown the formation of vessel-like structures in SVF-laden spheroids.

All publications, patents, and patent applications mentioned in this specification are herein incorporated by reference to the same extent as if each individual publication, patent, or patent application was specifically and individually indicated to be incorporated by reference, including the references set forth in the following list:

REFERENCE(S)

1. Nguyen, A., et al., Stromal vascular fraction: A regenerative reality? Part 1: Current concepts and review of the literature. Journal of Plastic, Reconstructive & Aesthetic Surgery, 2016. 69(2): p. 170-179.
2. Sheng, L., et al., Transplantation of stromal vascular fraction as an alternative for accelerating tissue expansion. Journal of plastic, reconstructive & aesthetic surgery: JPRAS, 2012.
3. Lauvrud, A. T., et al., Characterization of human adipose tissue-derived stem cells with enhanced angiogenic and adipogenic properties. J Tissue Eng Regen Med, 2016.
4. Nguyen, A., et al., Stromal vascular fraction: A regenerative reality? Part 1: Current concepts and review of the literature. J Plast Reconstr Aesthet Surg, 2016. 69(2): p. 170-9.
5. Mohammadi, R., et al., Nonexpanded Adipose Stromal Vascular Fraction Local Therapy on Peripheral Nerve Regeneration Using Allografts. J Invest Surg, 2016. 29(3): p. 149-56.
6. Premaratne, G. U., et al., Stromal Vascular Fraction Transplantation as an Alternative Therapy for Ischemic Heart Failure: Anti-inflammatory Role. Journal of Cardiothoracic Surgery, 2011. 6: p. 43-43.
7. Granel, B., et al., Safety, tolerability and potential efficacy of injection of autologous adipose-derived stromal vascular fraction in the fingers of patients with systemic sclerosis: an open-label phase I trial. Annals of the Rheumatic Diseases, 2015. 74(12): p. 2175-2182.
8. Comella, K., et al., Effects of the intramyocardial implantation of stromal vascular fraction in patients with chronic ischemic cardiomyopathy. Journal of Translational Medicine, 2016. 14: p. 158.
9. Atalay, S., A. Coruh, and K. Deniz, Stromal vascular fraction improves deep partial thickness burn wound healing. Burns, 2014. 40(7): p. 1375-1383.
10. Garcia-Olmo, D., et al., Treatment of enterocutaneous fistula in Crohn's Disease with adipose-derived stem cells: a comparison of protocols with and without cell expansion. International Journal of Colorectal Disease, 2009. 24(1): p. 27-30.

11. Menasche, P., Stem cells in the management of advanced heart failure. Curr Opin Cardiol, 2014.
12. Lai, C. Y., et al., Clearance kinetics of biomaterials affects stem cell retention and therapeutic efficacy. Biomacromolecules, 2014. 15(2): p. 564-73.
13. Cai, L., R. E. Dewi, and S. C. Heilshorn, Injectable Hydrogels with In Situ Double Network Formation Enhance Retention of Transplanted Stem Cells. Adv Funct Mater, 2015. 25(9): p. 1344-1351.
14. Patel, N. M., et al., Optimizing cell seeding and retention in a three-dimensional bioengineered cardiac ventricle: The two-stage cellularization model. Biotechnol Bioeng, 2016. 113(10): p. 2275-85.
15. Huang, C. C., et al., Enhancement of cell adhesion, retention, and survival of HUVEC/cbMSC aggregates that are transplanted in ischemic tissues by concurrent delivery of an antioxidant for therapeutic angiogenesis. Biomaterials, 2016. 74: p. 53-63.
16. Follin, B., et al., Human adipose-derived stromal cells in a clinically applicable injectable alginate hydrogel: Phenotypic and immunomodulatory evaluation. Cytotherapy, 2015. 17(8): p. 1104-18.
17. Silva, K. R., et al., Delivery of Human Adipose Stem Cells Spheroids into Lockyballs. PLoS One, 2016. 11(11): p. e0166073.
18. Burdick, J. A., R. L. Mauck, and S. Gerecht, To Serve and Protect: Hydrogels to Improve Stem Cell-Based Therapies. Cell Stem Cell, 2016. 18(1): p. 13-5.
19. Chen, Y. S., et al., Evaluation of a laminin-alginate biomaterial, adipocytes, and adipocyte-derived stem cells interaction in animal autologous fat grafting model using 7-Tesla magnetic resonance imaging. J Mater Sci Mater Med, 2017. 28(1): p. 18.
20. Natesan, S., et al., Adipose-Derived Stem Cell Delivery into Collagen Gels Using Chitosan Microspheres. Tissue Engineering. Part A, 2010. 16(4): p. 1369-1384.
21. Hoying, J. B., C. A. Boswell, and S. K. Williams, Angiogenic Potential of Microvessel Fragments Established in Three-Dimensional Collagen Gels. In Vitro Cellular & Developmental Biology. Animal, 1996. 32(7): p. 409-419.
22. Touroo, J. S., J. R. Dale, and S. K. Williams, Bioengineering human blood vessel mimics for medical device testing using serum-free conditions and scaffold variations. Tissue Eng Part C Methods, 2013. 19(4): p. 307-15.
23. Williams, S. K., et al., Encapsulation of adipose stromal vascular fraction cells in alginate hydrogel spheroids using a direct-write three-dimensional printing system. Biores Open Access, 2013. 2(6): p. 448-54.
24. Lin, S. D., et al., Injected Implant of Uncultured Stromal Vascular Fraction Loaded Onto a Collagen Gel: In Vivo Study of Adipogenesis and Long-term Outcomes. Ann Plast Surg, 2016. 76 Suppl 1: p. S108-16.
25. Aijian, A. P. and R. L. Garrell, Digital microfluidics for automated hanging drop cell spheroid culture. J Lab Autom, 2015. 20(3): p. 283-95.
26. Leung, B. M., et al., Media additives to promote spheroid circularity and compactness in hanging drop platform. Biomater Sci, 2015. 3(2): p. 336-44.
27. Chan, B. P., et al., Mesenchymal stem cell-encapsulated collagen microspheres for bone tissue engineering. Tissue Eng Part C Methods, 2010. 16.
28. Chan, O. C. M., K. F. So, and B. P. Chan, Fabrication of nano-fibrous collagen microspheres for protein delivery and effects of photochemical crosslinking on release kinetics. Journal of Controlled Release, 2008. 129(2): p. 135-143.
29. Keshaw, H., et al., Microporous collagen spheres produced via thermally induced phase separation for tissue regeneration. Acta Biomater, 2010. 6(3): p. 1158-66.
30. Yao, L., F. Phan, and Y. Li, Collagen microsphere serving as a cell carrier supports oligodendrocyte progenitor cell growth and differentiation for neurite myelination in vitro. Stem Cell Research & Therapy, 2013. 4(5): p. 109.
31. Yao, R., et al., Alginate and alginate/gelatin microspheres for human adipose-derived stem cell encapsulation and differentiation. Biofabrication, 2012. 4.
32. Yeo, M., et al., An Innovative Collagen-Based Cell-Printing Method for Obtaining Human Adipose Stem Cell-Laden Structures Consisting of Core-Sheath Structures for Tissue Engineering. Biomacromolecules, 2016. 17(4): p. 1365-1375.
33. Chang, C. C., et al., Direct-write Bioprinting Three-Dimensional Biohybrid Systems for Future Regenerative Therapies. Journal of biomedical materials research. Part B, Applied biomaterials, 2011. 98(1): p. 160-170.
34. Vernon, R. B., et al., Organized type I collagen influences endothelial patterns during "spontaneous angiogenesis in vitro": Planar cultures as models of vascular development. In Vitro Cellular & Developmental Biology-Animal, 1995. 31(2): p. 120-131.
35. Twardowski, T., et al., Type I collagen and collagen mimetics as angiogenesis promoting superpolymers. Curr Pharm Des, 2007. 13(35): p. 3608-21.
36. Klar, A. S., et al., Tissue-engineered dermo-epidermal skin grafts prevascularized with adipose-derived cells. Biomaterials, 2014. 35(19): p. 5065-78.
37. Klar, A. S., et al., Characterization of vasculogenic potential of human adipose-derived endothelial cells in a three-dimensional vascularized skin substitute. Pediatric Surgery International, 2016. 32(1): p. 17-27.
38. Cardoso, A. L., et al., Adipose tissue stromal vascular fraction in the treatment of full thickness burns in rats. Acta Cirurgica Brasileira, 2016. 31: p. 578-585.
39. Williams, S. K., M. A. Matthews, and R. C. Wagner, Metabolic studies on the micropinocytic process in endothelial cells. Microvasc Res, 1979. 18(2): p. 175-84.
40. Wagner, R. C., et al., Biochemical characterization and cytochemical localization of a catecholamine-sensitive adenylate cyclase in isolated capillary endothelium. Proc Natl Acad Sci USA, 1972. 69(11): p. 3175-9.
41. Wagner, R. C. and M. A. Matthews, The isolation and culture of capillary endothelium from epididymal fat. Microvasc Res, 1975. 10(3): p. 286-97.
42. Smith, C. M., et al., Three-dimensional bioassembly tool for generating viable tissue-engineered constructs. Tissue Eng, 2004. 10(9-10): p. 1566-76.
43. Smith, C. M., et al., Characterizing environmental factors that impact the viability of tissue-engineered constructs fabricated by a direct-write bioassembly tool. Tissue Eng, 2007. 13(2): p. 373-83.
44. Jarrell, B., et al., Human adult endothelial cell growth in culture. Journal of vascular surgery: official publication, the Society for Vascular Surgery [and] International Society for Cardiovascular Surgery, North American Chapter, 1984. 1(6): p. 757-64.
45. Shepherd, B. R., et al., Rapid perfusion and network remodeling in a microvascular construct after implantation. Arterioscler. Thromb.Vasc.Biol., 2004. 24(5): p. 898-904.
46. Sart, S., T. Ma, and Y. Li, Preconditioning stem cells for in vivo delivery. Biores Open Access, 2014. 3(4): p. 137-49.

47. Takemoto, N., et al., Transplantation of co-aggregates of Sertoli cells and islet cells into liver without immunosuppression. Transplantation, 2014. 97(3): p. 287-93.
48. Carter, W. B., et al., Stimulation of angiogenesis by canine parathyroid tissue. Surgery, 1996. 120(6): p. 1089-1094.
49. Cisneros Castillo, L. R., et al., Evaluation of Consistency in Spheroid Invasion Assays. Scientific Reports, 2016. 6: p. 28375.
50. Vernon, R. B. and M. D. Gooden, An improved method for the collagen gel contraction assay. In Vitro Cell Dev Biol Anim, 2002. 38(2): p. 97-101.
51. Madri, J. A. and S. K. Williams, Capillary endothelial cell cultures: phenotypic modulation by matrix components. Journal of Cell Biology, 1983. 97(1): p. 153-165.
52. Chang, R., et al., Biofabrication of a three-dimensional liver micro-organ as an in vitro drug metabolism model. Biofabrication, 2010. 2(4): p. 045004.
53. Chang, C. C., et al. In vitro patterned microvessels lose alignment in vivo. in Microcirculatory Society Meeting. 2010.
54. Chang, C. C., et al., Determinants of microvascular network topologies in implanted neovasculatures. Arteriosclerosis, thrombosis, and vascular biology, 2012. 32(1): p. 5-14.
55. Smith, C. M., et al., Three-dimensional bioassembly tool for generating viable tissue-engineered constructs. Tissue Eng, 2004. 10(9-10): p. 1566-76.
56. Smith, C. M., et al., Characterizing environmental factors that impact the viability of tissue-engineered constructs fabricated by a direct-write bioassembly tool. Tissue Eng, 2007. 13(2): p. 373-83.
57. Smith, C. M., et al., Automatic thresholding of three-dimensional microvascular structures from confocal microscopy images. J Microsc, 2007. 225(Pt 3): p. 244-57.
58. Chang, C. C., et al., Direct-write bioprinting three-dimensional biohybrid systems for future regenerative therapies. J Biomed Mater Res B Appl Biomater, 2011. 98(1): p. 160-70.
59. Nguyen, A., et al., Stromal vascular fraction: A regenerative reality? Part 1: Current concepts and review of the literature. Journal of Plastic, Reconstructive & Aesthetic Surgery, 2016. 69(2): p. 170-179.
60. Sheng, L., et al., Transplantation of stromal vascular fraction as an alternative for accelerating tissue expansion. Journal of plastic, reconstructive & aesthetic surgery: JPRAS, 2012.
61. Lauvrud, A. T., et al., Characterization of human adipose tissue-derived stem cells with enhanced angiogenic and adipogenic properties. J Tissue Eng Regen Med, 2016.
62. Nguyen, A., et al., Stromal vascular fraction: A regenerative reality? Part 1: Current concepts and review of the literature. J Plast Reconstr Aesthet Surg, 2016. 69(2): p. 170-9.
63. Mohammadi, R., et al., Nonexpanded Adipose Stromal Vascular Fraction Local Therapy on Peripheral Nerve Regeneration Using Allografts. J Invest Surg, 2016. 29(3): p. 149-56.
64. Nunes, S. S., et al., Generation of a functional liver tissue mimic using adipose stromal vascular fraction cell-derived vasculatures. Sci Rep, 2013. 3: p. 2141.
65. Premaratne, G. U., et al., Stromal Vascular Fraction Transplantation as an Alternative Therapy for Ischemic Heart Failure: Anti-inflammatory Role. Journal of Cardiothoracic Surgery, 2011. 6: p. 43-43.
66. Granel, B., et al., Safety, tolerability and potential efficacy of injection of autologous adipose-derived stromal vascular fraction in the fingers of patients with systemic sclerosis: an open-label phase I trial. Annals of the Rheumatic Diseases, 2015. 74(12): p. 2175-2182.
67. Comella, K., et al., Effects of the intramyocardial implantation of stromal vascular fraction in patients with chronic ischemic cardiomyopathy. Journal of Translational Medicine, 2016. 14: p. 158.
68. Atalay, S., A. Coruh, and K. Deniz, Stromal vascular fraction improves deep partial thickness burn wound healing. Burns, 2014. 40(7): p. 1375-1383.
69. Garcia-Olmo, D., et al., Treatment of enterocutaneous fistula in Crohn's Disease with adipose-derived stem cells: a comparison of protocols with and without cell expansion. International Journal of Colorectal Disease, 2009. 24(1): p. 27-30.
70. Menasche, P., Stem cells in the management of advanced heart failure. Curr Opin Cardiol, 2014.
71. Lai, C. Y., et al., Clearance kinetics of biomaterials affects stem cell retention and therapeutic efficacy. Biomacromolecules, 2014. 15(2): p. 564-73.
72. Cai, L., R. E. Dewi, and S. C. Heilshorn, Injectable Hydrogels with In Situ Double Network Formation Enhance Retention of Transplanted Stem Cells. Adv Funct Mater, 2015. 25(9): p. 1344-1351.
73. Patel, N. M., et al., Optimizing cell seeding and retention in a three-dimensional bioengineered cardiac ventricle: The two-stage cellularization model. Biotechnol Bioeng, 2016. 113(10): p. 2275-85.
74. Huang, C. C., et al., Enhancement of cell adhesion, retention, and survival of HUVEC/cbMSC aggregates that are transplanted in ischemic tissues by concurrent delivery of an antioxidant for therapeutic angiogenesis. Biomaterials, 2016. 74: p. 53-63.
75. Hiscox, A. M., et al., An islet-stabilizing implant constructed using a preformed vasculature. Tissue Eng Part A, 2008. 14(3): p. 433-40.
76. Follin, B., et al., Human adipose-derived stromal cells in a clinically applicable injectable alginate hydrogel: Phenotypic and immunomodulatory evaluation. Cytotherapy, 2015. 17(8): p. 1104-18.
77. Silva, K. R., et al., Delivery of Human Adipose Stem Cells Spheroids into Lockyballs. PLoS One, 2016. 11(11): p. e0166073.
78. Burdick, J. A., R. L. Mauck, and S. Gerecht, To Serve and Protect: Hydrogels to Improve Stem Cell-Based Therapies. Cell Stem Cell, 2016. 18(1): p. 13-5.
79. Chen, Y. S., et al., Evaluation of a laminin-alginate biomaterial, adipocytes, and adipocyte-derived stem cells interaction in animal autologous fat grafting model using 7-Tesla magnetic resonance imaging. J Mater Sci Mater Med, 2017. 28(1): p. 18.
80. Natesan, S., et al., Adipose-Derived Stem Cell Delivery into Collagen Gels Using Chitosan Microspheres. Tissue Engineering. Part A, 2010. 16(4): p. 1369-1384.
81. Lin, S. D., et al., Injected Implant of Uncultured Stromal Vascular Fraction Loaded Onto a Collagen Gel: In Vivo Study of Adipogenesis and Long-term Outcomes. Ann Plast Surg, 2016. 76 Suppl 1: p. S108-16.
82. Aijian, A. P. and R. L. Garrell, Digital microfluidics for automated hanging drop cell spheroid culture. J Lab Autom, 2015. 20(3): p. 283-95.
83. Leung, B. M., et al., Media additives to promote spheroid circularity and compactness in hanging drop platform. Biomater Sci, 2015. 3(2): p. 336-44.

84. Chan, B. P., et al., Mesenchymal stem cell-encapsulated collagen microspheres for bone tissue engineering. Tissue Eng Part C Methods, 2010. 16.
85. Chan, O. C. M., K. F. So, and B. P. Chan, Fabrication of nano-fibrous collagen microspheres for protein delivery and effects of photochemical crosslinking on release kinetics. Journal of Controlled Release, 2008. 129(2): p. 135-143.
86. Keshaw, H., et al., Microporous collagen spheres produced via thermally induced phase separation for tissue regeneration. Acta Biomater, 2010. 6(3): p. 1158-66.
87. Yao, L., F. Phan, and Y. Li, Collagen microsphere serving as a cell carrier supports oligodendrocyte progenitor cell growth and differentiation for neurite myelination in vitro. Stem Cell Research & Therapy, 2013. 4(5): p. 109.
88. Yao, R., et al., Alginate and alginate/gelatin microspheres for human adipose-derived stem cell encapsulation and differentiation. Biofabrication, 2012. 4.
89. Yeo, M., et al., An Innovative Collagen-Based Cell-Printing Method for Obtaining Human Adipose Stem Cell-Laden Structures Consisting of Core-Sheath Structures for Tissue Engineering. Biomacromolecules, 2016. 17(4): p. 1365-1375.
90. Vernon, R. B., et al., Organized type I collagen influences endothelial patterns during "spontaneous angiogenesis in vitro": Planar cultures as models of vascular development. In Vitro Cellular & Developmental Biology—Animal, 1995. 31(2): p. 120-131.
91. Twardowski, T., et al., Type I collagen and collagen mimetics as angiogenesis promoting superpolymers. Curr Pharm Des, 2007. 13(35): p. 3608-21.
92. Klar, A. S., et al., Tissue-engineered dermo-epidermal skin grafts prevascularized with adipose-derived cells. Biomaterials, 2014. 35(19): p. 5065-78.
93. Klar, A. S., et al., Characterization of vasculogenic potential of human adipose-derived endothelial cells in a three-dimensional vascularized skin substitute. Pediatric Surgery International, 2016. 32(1): p. 17-27.
94. Cardoso, A. L., et al., Adipose tissue stromal vascular fraction in the treatment of full thickness burns in rats. Acta Cirurgica Brasileira, 2016. 31: p. 578-585.
95. Bhang, S. H., et al., Mutual effect of subcutaneously transplanted human adipose-derived stem cells and pancreatic islets within fibrin gel. Biomaterials, 2013. 34(30): p. 7247-56.
96. Krishnan, L., et al., Cellular immunoisolation for islet transplantation by a novel dual porosity electrospun membrane. Transplantation proceedings, 2011. 43(9): p. 3256-61.
97. Knight, K. R., et al., Vascularized tissue-engineered chambers promote survival and function of transplanted islets and improve glycemic control. FASEB J., 2006.
98. Zhang, N., et al., Inhibition of angiogenesis is associated with reduced islet engraftment in diabetic recipient mice. Transplant.Proc., 2005. 37(10): p. 4452-4457.
99. Vajkoczy, P., et al., Angiogenesis and vascularization of murine pancreatic islet isografts. Transplantation, 1995. 60(2): p. 123-127.
100. Mendola, J. F., et al., Immunocytochemical study of pancreatic islet revascularization in islet isograft. Effect of hyperglycemia of the recipient and of in vitro culture of islets. Transplantation, 1994. 57(5): p. 725-30.
101. Williams, S. K., et al., Adipose Stromal Vascular Fraction Cells Isolated using an Automated Point of Care System Improve the Patency of ePTFE Vascular Grafts. Tissue engineering. Part A, 2013.
102. Krishnan, L., et al. Anchorage dependent persistent alignment of perfused microvasculature in implanted tissue constructs. in Proceedings of the ASME Bioengineering Conference. 2011.
103. Chang, C. C., et al., Angiogenesis in a microvascular construct for transplantation depends on the method of chamber circulation. Tissue Eng Part A, 2010. 16(3): p. 795-805.
104. Gruionu, G., et al., Encapsulation of ePTFE in prevascularized collagen leads to peri-implant vascularization with reduced inflammation. J Biomed Mater Res A, 2010. 95(3): p. 811-8.
105. Shepherd, B. R., et al., Rapid perfusion and network remodeling in a microvascular construct after implantation. Arterioscler.Thromb.Vasc.Biol., 2004. 24(5): p. 898-904.
106. Krishnan, L., et al., Vascularization and cellular isolation potential of a novel electrospun cell delivery vehicle. Journal of biomedical materials research. Part A, 2013.
107. Hiscox, A. M., et al., An Islet-Stabilizing Implant Constructed Using a Preformed Vasculature. Tissue Eng, 2007.
108. Leblanc, A. J., et al., Adipose stromal vascular fraction cell construct sustains coronary microvascular function after acute myocardial infarction. American journal of physiology. Heart and circulatory physiology, 2012. 302(4): p. H973-82.
109. Leblanc, A. J., et al., Microvascular Repair: Post-Angiogenesis Vascular Dynamics. Microcirculation, 2012.
110. Williams, S. K., L. B. Kleinert, and V. Patula-Steinbrenner, Accelerated neovascularization and endothelialization of vascular grafts promoted by covalently bound laminin type 1. Journal of biomedical materials research. Part A, 2011. 99(1): p. 67-73.
111. Kellar, R. S., et al., Three-dimensional fibroblast cultures stimulate improved ventricular performance in chronically ischemic canine hearts. Tissue engineering. Part A, 2011. 17(17-18): p. 2177-86.
112. Shepherd, B. R., J. B. Hoying, and S. K. Williams, Microvascular transplantation after acute myocardial infarction. Tissue Eng, 2007. 13(12): p. 2871-9.
113. Boswell, C. A. and S. K. Williams, Denucleation promotes neovascularization of ePTFE in vivo. J Biomater.Sci.Polym.Ed., 1999. 10(3): p. 319-329.
114. Balamurugan, A. N., et al., Bioartificial pancreas transplantation at prevascularized intermuscular space: effect of angiogenesis induction on islet survival. Pancreas, 2003. 26(3): p. 279-85.
115. Balamurugan, A. N., et al., Islet cell biology, regeneration, and transplantation. Int J Endocrinol, 2012. 2012: p. 139787.
116. Balamurugan, A. N. and T. L. Pruett, Trying to prevent the clogged drain: optimizing the yield and function of portal vein-infused islets. Dig Dis Sci, 2013. 58(5): p. 1170-2.
117. Lee, M., et al., Spheroform: therapeutic spheroid-forming nanotextured surfaces inspired by desert beetle Physosterna cribripes. Adv Healthc Mater, 2015. 4(4): p. 511-5.
118. Lima, A. C., et al., Fast and mild strategy, using superhydrophobic surfaces, to produce collagen/platelet lysate gel beads for skin regeneration. Stem Cell Rev, 2015. 11(1): p. 161-79.

119. Neto, A. I., et al., A novel hanging spherical drop system for the generation of cellular spheroids and high throughput combinatorial drug screening. Biomater Sci, 2015. 3(4): p. 581-5.
120. Leblanc, A. J., et al., Adipose-derived cell construct stabilizes heart function and increases microvascular perfusion in an established infarct. Stem Cells Transl Med, 2013. 2(11): p. 896-905.
121. Balamurugan, A. N., B. Ramakrishna, and S. Gunasekaran, Insulin secretory characteristics of monkey pancreatic islets: a simple method of islet isolation and the effect of various density gradients on separation. Diabetes Res Clin Pract, 2004. 66(1): p. 13-21.
122. Balamurugan, A. N., et al., Prospective and challenges of islet transplantation for the therapy of autoimmune diabetes. Pancreas, 2006. 32(3): p. 231-43.
123. Sutherland, D. E., et al., Islet autotransplant outcomes after total pancreatectomy: a contrast to islet allograft outcomes. Transplantation, 2008. 86(12): p. 1799-802.
124. Balamurugan, A. N., et al., Successful human islet isolation and transplantation indicating the importance of class 1 collagenase and collagen degradation activity assay. Transplantation, 2010. 89(8): p. 954-61.
125. Bellin, M. D., et al., Potent induction immunotherapy promotes long-term insulin independence after islet transplantation in type 1 diabetes. Am J Transplant, 2012. 12(6): p. 1576-83.
126. Balamurugan, A. N., et al., Identifying Effective Enzyme Activity Targets for Recombinant Class I and Class II Collagenase for Successful Human Islet Isolation. Transplant Direct, 2016. 2(1): p. e54.
127. Kidd, K. R. and S. K. Williams, Laminin-5-enriched extracellular matrix accelerates angiogenesis and neovascularization in association with ePTFE. J Biomed Mater Res A, 2004. 2004/04/02(2): p. 294-304.
128. Kidd, K. R., et al., Stimulated endothelial cell adhesion and angiogenesis with laminin-5 modification of expanded polytetrafluoroethylene. Tissue Engineering, 2005. 2005/11/02(9-10): p. 1379-1391.
129. Jarrell, B., et al., Human adult endothelial cell growth in culture. Journal of vascular surgery: official publication, the Society for Vascular Surgery [and] International Society for Cardiovascular Surgery, North American Chapter, 1984. 1(6): p. 757-64.
130. Nunes, S. S., et al., Implanted microvessels progress through distinct neovascularization phenotypes. Microvasc.Res., 2010. 79(1): p. 10-20.
131. Nunes, S. S., et al., Angiogenic potential of microvessel fragments is independent of the tissue of origin and can be influenced by the cellular composition of the implants. Microcirculation, 2010. 17(7): p. 557-67.
132. Herbst, T. J., et al., Differential effects of laminin, intact type IV collagen, and specific domains of type IV collagen on endothelial cell adhesion and migration. Journal of Cell Biology, 1988. 106(4): p. 1365-1373.
133. Nicosia, R. F. and A. Ottinetti, Modulation of microvascular growth and morphogenesis by reconstituted basement membrane gel in three-dimensional cultures of rat aorta: a comparative study of angiogenesis in matrigel, collagen, fibrin, and plasma clot. In Vitro Cell Dev Biol, 1990. 26(2): p. 119-28.
134. Peterson, A. W., et al., Vasculogenesis and Angiogenesis in Modular Collagen-Fibrin Microtissues. Biomater Sci, 2014. 2(10): p. 1497-1508.
135. Gu, Y., et al., Development of a new method to induce angiogenesis at subcutaneous site of streptozotocin-induced diabetic rats for islet transplantation. Cell Transplant, 2001. 10(4-5): p. 453-7.
136. Williams, S. K., M. A. Matthews, and R. C. Wagner, Metabolic studies on the micropinocytic process in endothelial cells. Microvasc Res, 1979. 18(2): p. 175-84.
137. Wagner, R. C., et al., Biochemical characterization and cytochemical localization of a catecholamine-sensitive adenylate cyclase in isolated capillary endothelium. Proc Natl Acad Sci USA, 1972. 69(11): p. 3175-9.
138. Wagner, R. C. and M. A. Matthews, The isolation and culture of capillary endothelium from epididymal fat. Microvasc Res, 1975. 10(3): p. 286-97.
139. Loganathan, G., et al., Culture of impure human islet fractions in the presence of alpha-1 antitrypsin prevents insulin cleavage and improves islet recovery. Transplant Proc, 2010. 42(6): p. 2055-7.
140. Balamurugan, A. N., et al., Islet product characteristics and factors related to successful human islet transplantation from the Collaborative Islet Transplant Registry (CITR) 1999-2010. Am J Transplant, 2014. 14(11): p. 2595-606.
141. Foty R. I. J Vis Exp. 2011 May 6; (51). pii: 2720. doi: 10.3791/2720. A simple hanging drop cell culture protocol for generation of 3D spheroids.

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. A method of making a spheroid comprising one or more cell or tissue, comprising the steps of:
providing a suspension comprising one or more cell or tissue selected from the group consisting of stromal vascular fraction, microvascular fragment and stem cell; optionally comprising one or more cells appropriate for repair, restructure or repopulation of a tissue or organ, magnetic beads or combinations thereof; dispersed within a biocompatible medium comprising collagen or fibrin;
depositing a triblock copolymer onto a super-hydrophobic surface to form a hydrophilic surface on the super-hydrophobic surface, wherein the triblock copolymer has an amphiphilic block structure which gives it hydrophilic and hydrophobic properties; and
bioprinting a droplet of the suspension atop the hydrophilic surface to form a spheroid, and incubating the spheroid in an aqueous solution to dissolve the triblock copolymer to remove the spheroid from the super-hydrophobic surface, thereby obtaining the spheroid comprising one or more cell or tissue.

2. The method of claim 1, wherein the biocompatible medium is a hydrogel.

3. The method of claim 2, wherein the hydrogel comprises collagen type I.

4. The method of claim 1, wherein the one or more stromal vascular fraction, microvascular fragment and stem cell are derived from adipose tissue.

5. The method of claim 1, wherein the one or more cell appropriate for repair, restructure or repopulation of a tissue or organ are pancreatic islets and/or islet cells.

6. The method of claim 1, wherein the step of bioprinting the droplet of the suspension comprises direct-write printing the suspension.

7. The method of claim 1, wherein the super-hydrophobic surface has a water contact angle of greater than about 150°.

8. The method of claim 7, wherein the water contact angle is about 150° to about 170°.

9. The method of claim 1, wherein the step of bioprinting the droplet comprises bioprinting a droplet having a diameter of about 0.2 mm to about 5 mm.

10. The method of claim 1, further comprising the step of incubating the spheroids at physiological temperatures for a suitable period of time subsequent to bioprinting the droplet.

11. The method of claim 1, further comprising the step of culturing the spheroids in a cell culture medium subsequent to bioprinting the droplet.

12. The method of claim 1, wherein the stem cell is embryonic stem cell, adult stem cell, or pluripotent stem cell.

13. A method of making a spheroid suitable for implantation into a subject in need thereof, comprising the steps of:
- providing a suspension comprising one or more cells or tissues selected from the group consisting of stromal vascular fraction, microvascular fragment and stem cell; and
- one or more cells appropriate for repair, restructure or repopulation of a tissue or organ selected from the group consisting of neuron, cardiomyocyte, myocyte, vascular smooth muscle cell, gastrointestinal smooth muscle cell, chondrocyte, pancreatic acinar cell, islets of Langerhans, islet beta cell, osteocyte, hepatocyte, Kupffer cell, fibroblast, myoblast, satellite cell, endothelial cell, adipocyte, preadipocyte and biliary epithelial cell;
- wherein said one or more cells or tissues and said one or more cells appropriate for repair are dispersed within a biocompatible medium comprising collagen or fibrin;
- depositing an amount of a triblock copolymer on a defined area of the super-hydrophobic surface to form a hydrophilic surface, wherein the triblock copolymer has an amphiphilic block structure which gives it hydrophilic and hydrophobic properties; and
- bioprinting a droplet of the suspension atop the hydrophilic surface to form a spheroid, and incubating the spheroid in an aqueous solution to dissolve the triblock copolymer to remove the spheroid from the super-hydrophobic surface, thereby obtaining the spheroid comprising one or more cell or tissue.

14. The method of claim 13, wherein the super-hydrophobic surface has a water contact angle of about 150° to about 170°.

15. The method of claim 13, wherein the biocompatible medium comprises collagen type I.

16. A method of making a spheroid including a mixture of cells, comprising the steps of:
- preparing a hydrogel suspension of the mixture of cells, wherein the cells comprise stromal vascular cells from an adipose stromal vascular fraction and intact pancreatic islets or islet cells, wherein the hydrogel suspension comprises collagen or fibrin;
- depositing an amount of a triblock copolymer on a defined area of a super-hydrophobic surface to form a hydrophilic surface, wherein the triblock copolymer has an amphiphilic block structure which gives it hydrophilic and hydrophobic properties; and
- bioprinting a droplet of the hydrogel suspension of the mixture of cells atop the hydrophilic surface to form a spheroid, and incubating the spheroid in an aqueous solution to dissolve the triblock copolymer to remove the spheroid from the super-hydrophobic surface, thereby obtaining the spheroid comprising one or more cell or tissue.

17. The method of claim 1, wherein the one or more cells appropriate for repair, restructure or repopulation of a tissue or organ are selected from the group consisting of neurons, cardiomyocytes, myocytes, vascular and/or gastrointestinal smooth muscle cells, chondrocytes, pancreatic acinar cells, islets of Langerhans, islet beta cells, osteocytes, hepatocytes, Kupffer cells, fibroblasts, myoblasts, satellite cells, endothelial cells, adipocytes, preadipocytes and biliary epithelial cells.

18. The method of claim 16, wherein the hydrogel suspension comprises collagen type 1.

19. The method of claim 13, wherein the stem cell is embryonic stem cell, adult stem cell, or pluripotent stem cell.

* * * * *